United States Patent [19]

Riess et al.

[11] Patent Number: 5,679,459
[45] Date of Patent: Oct. 21, 1997

[54] PERFLUORINATED AMPHIPHILIC PHOSPHOROUS COMPOUNDS: LIPOSOMAL COMPOSITIONS

[75] Inventors: Jean G. Riess; Jacques Greiner; Alain Milius; Pierre Vierling; Frederic Guillod; Sylvie Gaentzler, all of Nice, France

[73] Assignee: Alliance Pharmaceutical Corp., San Diego, Calif.

[21] Appl. No.: 467,467

[22] Filed: Jun. 6, 1995

Related U.S. Application Data

[62] Division of Ser. No. 893,227, Jun. 3, 1992.

[51] Int. Cl.$^6$ .......................... A61K 9/127; B01F 17/14; C07F 9/02
[52] U.S. Cl. .......................... 428/402.2; 252/312; 252/351; 514/51; 514/975; 554/81; 424/450; 558/186
[58] Field of Search .......................... 252/312, 351; 514/78, 832, 833, 938, 975; 536/17.1, 117; 558/186; 424/450; 428/402.2; 554/81

[56] References Cited

U.S. PATENT DOCUMENTS

| | | | |
|---|---|---|---|
| 2,026,785 | 1/1936 | Harris | 252/351 X |
| 2,052,029 | 8/1936 | Harris | 252/351 X |
| 4,814,112 | 3/1989 | Paltauf et al. | 554/81 |
| 4,914,197 | 4/1990 | Yamamoto et al. | 536/117 |
| 4,942,179 | 7/1990 | Borgarello et al. | 514/832 X |
| 4,985,550 | 1/1991 | Charpiot et al. | 536/18.4 |
| 5,061,484 | 10/1991 | Heldebrant | 424/450 |
| 5,080,833 | 1/1992 | Ishimori | 436/518 |
| 5,169,635 | 12/1992 | Ono et al. | 424/450 |
| 5,344,930 | 9/1994 | Riess et al. | 558/186 X |

FOREIGN PATENT DOCUMENTS

| | | |
|---|---|---|
| 0255443 | 2/1988 | European Pat. Off. . |
| 0311473 | 4/1989 | European Pat. Off. . |
| 2405042 | 8/1975 | Germany . |
| 9015807 | 12/1990 | WIPO . |

OTHER PUBLICATIONS

Chemical Abstracts, vol. 115, No. 24, 9 Dec. 1991, Columbus, Ohio, US; abstract no. 256478J, C. Santaella et al.: New perfluoroalkylated phospholipids as injectable surfactants: synthesis, preliminary physicochemical and bicompatability data. pp. 901; col. 1; see New Journal of Chemistry vol. 15, No. 8–9, 1991, Paris pp. 685–692.

Chemical Abstracts, vol. 113, No. 25, 17 Dec. 1990, Columbus, Ohio, US; abstract no. 232139G, K. Ogawa et al.: The reaction of epoxy compounds with phosphates. I. synthesis and physicochemical properties of amphiphilic phosphate salt monomers sodium . . . pp. 4; col. 2; see abstract & Nippon Kagaku Kaisha vol. 1990, No. 9, 1990, Japan pp. 955–961.

Chemical Abstracts, vol. 110, No. 17, 24 Apr. 1989, Columbus, Ohio, US; abstract no. 154749C, J. Gu et al.: Synthesis of fluorocarbon phospholipids and the formation of their liposomes. pp. 767; col. 2; see abstract & Huacue Xuebao vol. 46, No. 9, 1988; Shanghai pp. 913–918.

Chemical Abstracts, vol. 109, No. 1, 4 Jul. 1988, Columbus, Ohio, US; abstract no. 6733G, J. Wakatsuki: Preparations of fluoroalkyl phosphate esters as synthetic liposomes. pp. 639; col. 2; see abstract & JP.A.62 195 390 (Kao Corporation) 28 Aug. 1987.

*Primary Examiner*—Richard D. Lovering
*Attorney, Agent, or Firm*—Knobbe, Martens Olson & Bear

[57] ABSTRACT

Perfluoroalkylated amphiphilic phosphorus compounds, corresponding to the formulae:

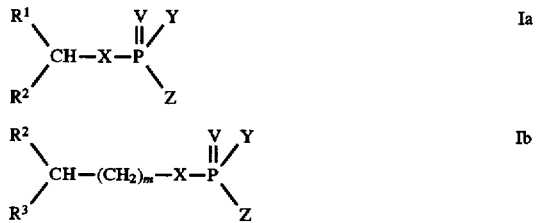

wherein

V is O or S;

$R^1$, $R^2$ and $R^3$ are H or substituted or unsubstituted perfluoroalkylated or hydrocarbon radicals;

provided that $R^1$, $R^2$ or $R^3$ is a perfluoroalkylated radical; and Y and Z are radicals which can bear a part derived from a sugar, a polyol, or a hydrophilic polymer such as polyethyleneglycol, a perfluoroalkylated part or a part derived from a pharmaceutically active molecule, and method for their preparation and use. These compounds can be included in preparations, emulsions, dispersions, gels, microemulsions, notably for biomedical uses.

4 Claims, 8 Drawing Sheets

PERFLUORINATED AMPHIPHILIC PHOSPHOROUS COMPOUNDS: LIPOSOMAL COMPOSITIONS

This application is a divisional of U.S. patent application Ser. No. 07/893,227, allowed filed Jun. 3, 1992.

BACKGROUND OF THE INVENTION

This application claims priority to French application No. 91/06798, filed Jun. 5, 1991. Fluorocarbons are preferably used as oxygen carriers, because these compounds are very inert and dissolve high concentrations of gases. However, fluorocarbons must be introduced into the vascular system in a dispersed form, for example as an emulsion, because fluorocarbons are insoluble in water. A surfactant or a combination of surfactants are necessary to achieve a stable fluorocarbon dispersion in water.

One fluorocarbon emulsion in biomedical use is Fluosol-DA 20% or Fluosol, developed by the Green Cross Corp. in Japan. Other more highly concentrated fluorocarbon emulsions are also known, such as those described by C. Long, D. Long, J. G. Riess, R. Follana, A. Burgan and R. Mattrey in "Blood Substitutes", edited by T. M. S. Chang and R. P. Geyer (Marcel Dekker Inc. NY, 1989), pp. 441–442. These fluorocarbon emulsions have certain drawbacks, for the surfactants used are not particularly adapted to the emulsification of fluorocarbons, and do not allow the modulation of the emulsions' characteristics in order to adapt them to specific therapeutic applications. A further, ideal, objective would be the ability to modulate the biological response they trigger in the organism.

Likewise it is desirable to gain further mastery in the art of liposome technology, especially to allow the modulation of the characteristics and properties of lipid membranes and liposomes and to extend their spectrum of applications, especially for drug and contrast-agent delivery.

Thus, research has been undertaken to find new surfactants and/or cosurfactants which are biocompatible, and better adapted to the emulsification of fluorocarbons than those used at present.

Following this research, it has been found that fluorinated polyhydroxylated compounds and fluorinated derivatives of amino acids could be used in this aim, as described in EP-A-0 255 443 and EP-A- 0 311 473; but these derivatives are not phosphorus-based compounds.

More recently, amphiphilic molecules containing phosphorus and fluorine have been prepared, as described in WO 90/15807, but the compounds described therein have in their hydrophilic part neither a polyhydroxylated derivative nor a highly polymerized polyethoxylated motif.

It is therefore an object of the invention to develop more effective surfactants specifically suited to providing dispersions or emulsions of fluorocarbons that are particularly suitable for biological use.

SUMMARY OF THE INVENTION

The invention provides perfluorinated amphiphilic phosphorus compounds of the formulae Ia and Ib, comprising a substituted phosphate group joined by a bridging group, X, as defined below, to a substituted methyl group. The methyl group is substituted with radicals $R^1$, $R^2$, and $R^3$, which are defined below and can comprise fluorinated or perfluorinated alkyl radicals, or hydrocarbon radicals, and the phosphate group is substituted with radicals Y and Z, which are defined below. Y can be substituted in part with a radical $R^8$, to comprise in whole of in part, sugars, polyols, or a highly polymerized polyethylene glycol moiety, to form a hydrophilic head. The amphiphilic molecule can further comprise a radical derived from a therapeutic agent, incorporated into Z. The thus substituted phosphate group comprises a hydrophilic head group in association with a negative charge. In preferred embodiments $R^1$, $R^2$, and X can be substituted with $R_F$, as defined below, which is selected from a group of fluorinated and perfluorinated groups, to form a perfluoroalkylated hydrophobic group. The fluorinated radicals of the amphiphilic molecule can also be substituted with chlorine or bromine atoms. In preferred embodiments, the hydrophilic head group comprises a radical $R^8$, which is glucose, mannose, galactose, sucrose, trehalose, maltose, or xylitol.

In a particularly preferred embodiment, the compound of the invention is an ((F-alkyl)alkyl)(pentosyl)phosphate, for example, (2-(F-alkyl)ethyl)(6-D-glucosyl)phosphate. In other preferred embodiments, an amphiphilic compound of the invention is a (2,3-di-O-(3-F-alkyl)alkanoyl)-1-glyceryl-(6-D-glucosyl)phosphate, for example, 2,3-di-O-(3-(F-hexyl)propanoyl)-1-glyceryl)(6-D-glucosyl)phosphate. In yet another preferred embodiment, an amphiphilic compound of the invention is a bis(2-(F-hexyl)alkyl)(6-D-pentosyl)phosphate, for example, bis(2-(F-hexyl)ethyl)(6-D-glucosyl)phosphate.

According to another aspect of the invention there are provided compositions for biomedical use, comprising at least one of the compounds of the invention. In a preferred embodiment, the composition further comprises a marker element. In yet another composition according to the invention, the Z radical of the amphiphilic molecule contains a biologically active substance. The compositions can contain an amphiphilic molecule of the invention incorporated into vesicles or liposomes. In a preferred embodiment of this type, the composition comprises liposomes formed of perfluoroalkylated phospholipids.

In yet other embodiments, there are provided emulsions of a fluorocarbon comprising one of the amphiphilic compounds of the invention. The emulsion can further comprise an aqueous phase and a surfactant in addition to an oily phase. In a preferred embodiment, the oily phase is a highly fluorinated or perfluorinated compound. The surfactant in the emulsion can include phospholipids. A preferred phospholipid is lecithin. The surfactant can also be a copolymer of polyoxyethylene or polyoxypropylene. In other preferred embodiments, the oily phase can comprise an F-alkyl substituted ethene, ether, decalin, nonane, or methyl quinolidine. The emulsion preferably contains from about 0.01% to 30% w/v of an amphiphilic compound of the invention and from about 10% to 125% oily phase. The emulsions disclosed are useful in modifying intravascular persistence, the biodistribution and/or the recognition of particles constituting disperse systems such as emulsions, microemulsions, and liposomes, and the specific cell tissue targeting to these particles.

DETAILED DESCRIPTION OF THE INVENTION

Figure 1A:
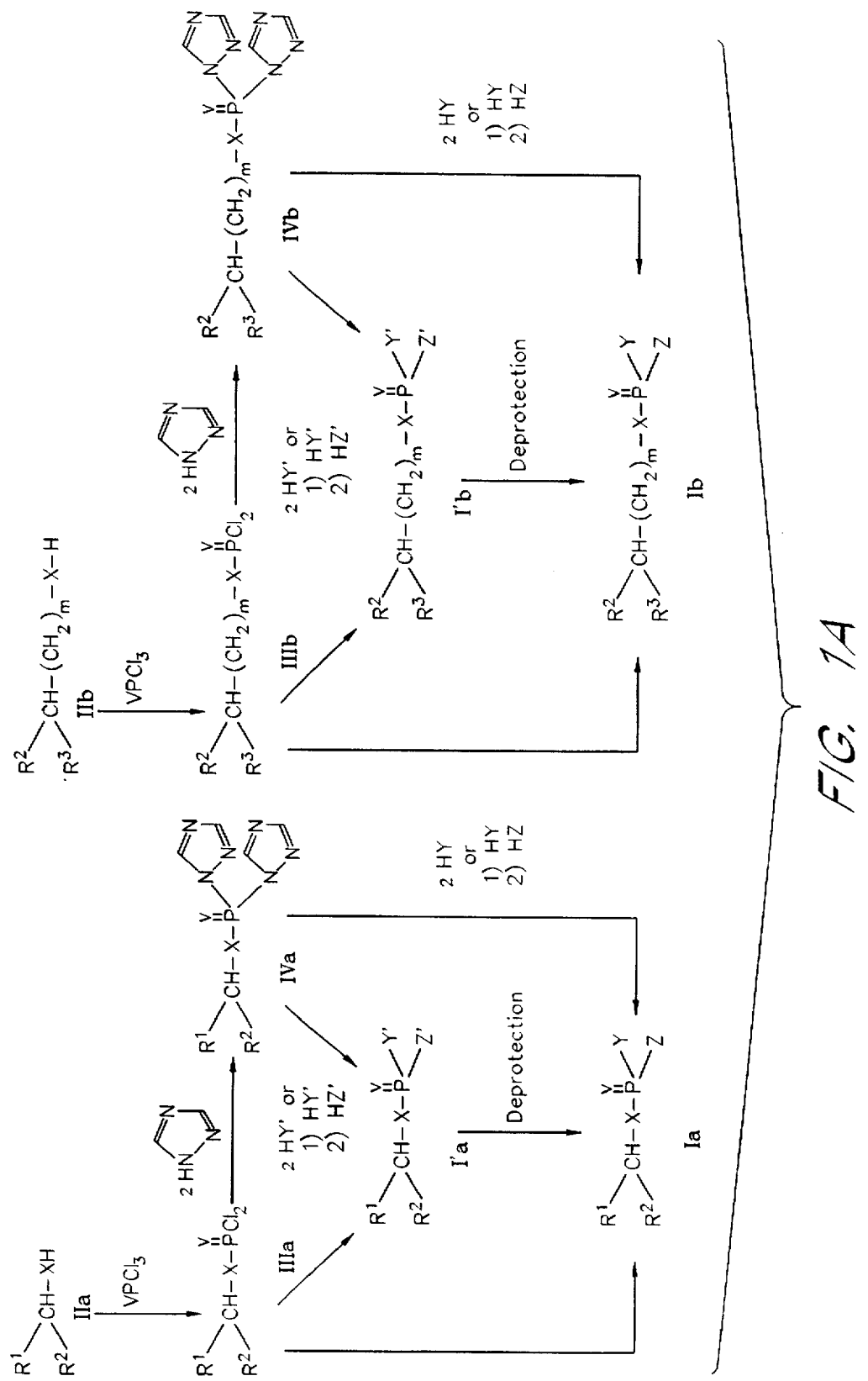
FIG. 1a sets forth a general synthetic scheme (Method 1) for the preparation of compounds having the general formula Ia and Ib.

The present invention provides new amphiphilic compounds of phosphorus, containing a highly fluorinated substituent, their preparation procedure and their use, in particular in preparations for biomedical applications. These compounds can be used, in particular as emulsifying agents, in emulsions destined to be used in the biomedical field, for example as oxygen or contrast agents carriers, for intravascular or other types of administration. Another application is their use in the preparation of vesicles or of liposomal formulations as transport and delivery systems of therapeutic active agents.

Among these compositions for biomedical use can be cited those based on fluorocarbons which can be used as blood substitutes, for treating cerebral and cardiac ischemia, in percutaneous transluminal coronary angioplasty, as cardioplegic and reperfusion solutions, as well as in preparations for sensibilizing tumors to radiation or to chemotherapeutic agents, for the preservation of organs and isolated tissues, for ventriculo-subarachnoid perfusion of the brain and for diagnosis by medical imagery.

The present invention concerns new amphiphilic perfluoroalkylated phosphorus compounds bearing different hydrophilic heads, which can be used in dispersed systems, including fluorocarbon emulsions, and in liposome manufacturing and technology. The choice, in particular, of a hydrophilic head derived from a sugar or a highly polymerized polyethylene glycol moiety connected to a perfluoroalkylated hydrophobic part through a phosphorus-based group, allows increased hydrophilic and amphiphilic character, and modulation of the biological properties and more particularly the biodistribution, intravascular persistence, molecular recognition and tissue targeting of fluorocarbon emulsions and liposome formulations. The phosphate group also allows the introduction of a negative charge simultaneously with the highly fluorinated fragment, the sugar and the polymerized polyethylene glycol moieties. Negatively charged and/or polyethylene embedded liposomes, for example, are known to prolong the intravascular persistance and to modify the biodistribution. The sugar moiety is important in the biodistribution and targeting process, e.g., for the mannose derivative it was observed that alveolar, peritoneal macrophages and blood monocytes of various mammalian species express on the surface of a mannose receptor with high affinity for a specific sugar mannose. This receptor mediates efficient internalization of the perfluoroalkylated amphiphiles, especially when the amphiphiles bear a pharmaceutically active compound. The pharmaceutically active compound will be fixed onto the molecule by a chemical bond, for example, a covalent bond on the phosphoric group.

According to the invention, the compound corresponds to one of the general formulae:

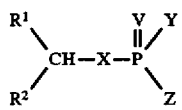

Ia

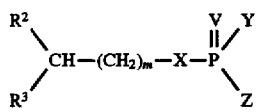

Ib wherein

1) V represents O or S,

2) —X— represents —O—, —S—, or —NR$^4$— with R$^4$ representing a hydrogen atom, a linear or branched hydrocarbon saturated or unsaturated radical, in $C_1$ to $C_{24}$, or a radical of formula $R_F(CH_2)_a$ W wherein a is an integer from 0 to 12, $R_F$ is a fluorinated alkylated radical of 2 to 23 carbon atoms, wherein 50 to 100% of the hydrogen atoms have been replaced by fluorine atoms, $R_F$ can bear other substituents chosen from among Cl and Br, and $R_F$ includes at least 4 fluorine atoms, and W represents —(CH=CH)$_d$—(CH$_2$)$_e$—(CH=CH)$_f$—(CH$_2$)$_g$—, where d is an integer from 0 to 12, e is an integer from 0 to 11, f is an integer from 0 to 12, g is an integer from 0 to 11, with d+f=0 to 12, and e+g=0 to 11,
—OCH$_2$CH(CH$_2$OH)CH$_2$—, or
—OCH$_2$CH(CH$_2$OH)—, 3) m is an integer from 1 to 20, 4) R$^1$ represents a radical chosen from among the radicals of formula:

$R_F$
$R_F$—(CH$_2$)$_a$—W—A—(CH$_2$)$_b$—,
$R_F$(CH(CH$_3$)CH$_2$O)$_c$—CH$_2$—
$R_F$—(CH$_2$CH$_2$O)$_c$—CH$_2$—,
$R_F$—(CH$_2$CH$_2$S)$_c$—CH$_2$—, and
$R_F$—W— wherein a, $R_F$ and W are as defined above, b is an integer from 1 to 12, c is an integer from 1 to 12, and A represents —O—,
—S—,
—OC(O)—,
—C(O)O—,
—(R$^5$)N— or —(R$^5$)(R$^6$)N$^+$— with R$^5$ and R$^6$ representing a hydrogen atom, a linear or branched, hydrocarbon radical, saturated or unsaturated in $C_1$ to $C_{24}$, the hydroxyethyl radical or the $R_F(CH_2)_a$W radical with $R_F$, a and W such as defined above,
—(CH$_2$)$_n$— wherein n=0 or 1,
—C(O)N(R$^5$)—(CH$_2$)$_s$—B— with R$^5$ such as defined above, s=1 to 12, and B representing —O—, —OC(O)— or —C(O)O—,
—C(O)N(R$^7$)—(CH$_2$)$_r$— or —N(R$^7$)C(O)(CH$_2$)$_r$— with r=1 to 12 and R$^7$ representing a hydrogen atom, a linear or branched hydrocarbon radical, saturated or unsaturated in $C_1$ to $C_{24}$, the hydroxyethyl radical or the $R_F(CH_2)_a$W— radical with $R_F$, W and a as defined above.

5) R$^2$ represents
a hydrogen atom, $R^1$—,
$R_H$—W—A—$(CH_2)_b$—,
$R_H$—$(CH_2CH_2O)_c$—$CH_2$—,
$R_H$—$(CH(CH_3)CH_2O)_c$—$CH_2$—, or
$R_H$—$(CH_2CH_2S)_c$—$CH_2$—, with $R_H$ representing a hydrogen atom or a linear or branched hydrocarbon chain, saturated or unsaturated in $C_1$ to $C_{20}$, and W, A, b and c having the above signification.

6) $R^3$ represents a radical chosen from among the radicals of formulae
$R_F$—,
$R_F$—$(CH_2)_a$—W—A—,
$R_F$—$(CH_2CH_2O)_c$—,
$R_F$—$(CH(CH_3)CH_2O)_c$—,
$R_F$—$(CH_2CH_2S)_c$—,
$R_F$—W—,
$R_H$—W—A—,
$R_H$—$(CH_2CH_2O)_c$—,
$R_H$—$(CH(CH_3)CH_2O)_c$—,
$R_H$—$(CH_2CH_2S)_c$—, wherein $R_F$, a, W, A, c and $R_H$ have the above signification, on condition that at least one of $R^2$ and $R^3$ of formula (Ib) bears an $R_F$ part.

7) Y represents a radical chosen from among the radicals of formula:
—$X^1(CH_2)_{a'}X^2(R^8)$,
—$X^1(R^8)$, wherein a' is an integer from 2 to 12, $X^1$ and $X^2$ independently represent —O—, —S— or —N($R^9$)— with $R^9$ a hydrogen atom, a linear or branched hydrocarbon radical, saturated or unsaturated, in $C_1$ to $C_{24}$, and $R^8$ represents a radical derived — from a sugar of the tetrose, pentose, hexose, aminopentose, aminohexose, deoxypentose, deoxyhexose, disaccharide and oligosaccharide series,
— from a cyclic hexitol,
— from a polyol consisting of the hydrogenated form of a sugar of the tetrose, pentose, hexose, aminopentose, aminohexose, deoxypentose, deoxyhexose, disaccharide and oligosaccharide series,
— from the sugars and polyols mentioned above wherein one or several hydrogen atoms of the OH polyol or sugar groups have been replaced by an acetyl, benzyl, allyl, benzoyl, trityl, isopropylidene, benzylidene, cyclohexylidene group, by a group of formula $(CH_2CH_2O)_pR^9$ with p an integer from 1 to 100 and $R^9$ as defined above, or by an $R^1$ group as defined above,

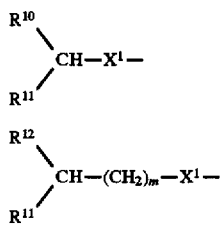

wherein m and $X^1$ are as defined above, $R^{10}$ and $R^{11}$ which may be identical or different represent $R^2$ as defined above, $R^{12}$ represents $R^3$ as defined above,
—OH
—OM with M representing an organic or inorganic cation, —O$(CH_2CH_2O)_pR^9$
—O$(CH(CH_3)CH_2O)_qR^9$, or
—O$(CH_2CH_2O)_q$—$(CH(CH_3)CH_2O)_{q'}$—$(CH_2CH_2O)_{q''}$—$R^9$ wherein $R^9$ is as defined above, and p, q, q' and q" are integers from 1 to 100, and 8) Z represents a radical chosen from among the radicals of formula:
—$X^1(CH_2)_{a'}$—$X^2(R^8)$,
—$X^1(R^8)$,
—OH,
—OM,
—O$(CH_2CH_2O)_pR^9$,
—O$(CH(CH_3)CH_2O)_qR^9$,
—O$(CH_2CH_2O)_q$—$(CH(CH_3)CH_2O)_{q'}$—$(CH_2CH_2O)_{q''}$—$R^9$,
—O$CH_2CH(OH)CH_2OH$,
—N$(R^{14})(R^{15})$,
—O$(CH_2)_{d'}$—W¹, and
$X^2R^{17}$ wherein $X^1$, $X^2$, $R^8$, $R^9$, a', p, q, q' and q" are as defined above, — $R^{14}$ and $R^{15}$ represent independently a hydrogen atom, a linear or branched alkyl group in $C_1$ to $C_4$, —$(CH_2CH_2O)_bR^9$, b' is an integer from 1 to 5, or $R^{14}$ and $R^{15}$ together form —$(CH_2)_{c'}$ with c' an integer from 2 to 5, or $R_{14}$ and $R_{15}$ together form with the nitrogen atom a morpholino group — W' represents an acetic 2-amino group, —N($R^{14}$)($R^{15}$), or —N⁺($R^{14}$)($R^{15}$)($R^{16}$) with $R^{14}$ and $R^{15}$ such as defined above, and $R^{16}$ identical or different with the same definition as $R^{14}$ or representing a radical derived from an active therapeutic agent, — d' is an integer from 1 to 5, and
— $R^{17}$ is a radical derived from a pharmaceutically active molecule, on condition that 1. Y and Z do not both represent —OH, —OM or —O$(CH_2CH_2O)_pR^9$ for p=1 to 5,
2. Z does not represent
—OH,
—OM,
—N($R^{14}$)($R^{15}$),
—O—$(CH_2)_{d'}$—W', or
—O—$CH_2$—CH(OH)—$CH_2OH$,
when Y is

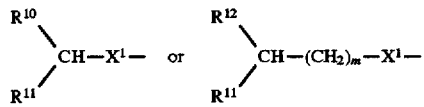

3. and Z does not represent
—N($R^{14}$)($R^{15}$),
—O—$(CH_2)_{d'}$—W', or
—O—$CH_2$—CH(OH)—$CH_2OH$,
when Y represents OH, OM, or O$(CH_2CH_2O)_pR^9$ for p=1 to 5.

In the compounds of formula (Ia) or (Ib) of the invention, the presence of a perfluoroalkylated part $R_F$ makes is possible to confer on the compound, not only hydrophobic and fluorophilic properties, but also a better biocompatibility, for example avoiding a hemolytic action detectable on human red blood cells, even at concentrations above 50 g/L. The choice of a phosphate-type connector, in the form of a diester, between the fluorophilic part and the sugar-type polar head makes it possible to confer emulsifying properties on the fluorocarbons, which show a distinct improvement over those of the compounds disclosed by EP-A-0-255443. The choice of an intermediate phosphate-type group, in the form of a phosphodiester or phosphotriester, also makes available, at the other end of the compound, strongly hydrophilic groups which can contain, as well, a pharmaceutical substance, an element or a fragment that can serve as marker, fixed by a covalent bond onto this hydrophilic extremity.

Thus the compounds of the invention can be used as vectors of drugs, of active principals or of markers.

According to the invention, the fluorinated alkyl radicals $R_F$ to be used can be chosen from among radicals of formulae:

(a) $F(CF_2)_i$— wherein i is an integer from 2 to 12, (b) $(CF_3)_2CF—(CF_2)_j$— wherein j is an integer from 0 to 8, (c) $R_{F1}(CF_2CF(CF_3))_k$— wherein $R_{F1}$ represents $CF_3$—, $C_2F_5$— or $(CF_3)_2CF$— and k is an integer from 1 to 4, (d) $(R_{F2})(R_{F3})CFO(CF_2—CF_2)_l$— wherein $R_{F2}$ and $R_{F3}$ represent independently $CF_3$—, $C_2F_5$—, n—$C_3F_7$— or $CF_3CF_2CF(CF_3)$—, or $R_{F2}$ and $R_{F3}$ together form —$(CF_2)_4$— or —$(CF_2)_5$—, and l is an integer from 1 to 6.

(e) $CF_3CF_2O(CF_2CF_2O)_tCF_2$— wherein t is an integer from 0 to 5, (f) $CF_3(CF_2)_2O(CFCF_3)CF_2O)_u$—$CF(CF_3)$— wherein t is an integer from 0 to 6, and the radicals of paragraphs (a) to (f) wherein one or several fluorine atoms are replaced by one or several hydrogen, chlorine or bromine atoms, provided that at least 50% of the atoms bound to the $R_F$ carbon skeleton be fluorine atoms and $R_F$ contain at least 4 fluorine atoms.

In the above general formulae, hydrocarbon radicals apply to radicals derived from saturated, monounsaturated and polyunsaturated hydrocarbons, the unsaturation may be ethylenic or acetylenic, and the radicals either linear or branched.

When in the above formula Y or Z represents —$X^1(CH_2)_a$ $X^2(R^8)$ or —$X^1(R^8)$, with $R^8$ representing a radical derived from a sugar, the sugars derived from the tetrose series can be, for example, erythrose or threose; the sugars of the pentose series can be arabinose, lyxose, ribose, xylose or fructose; the sugars belonging to the hexose series can be allose, altrose, galactose, glucose, gulose, idose, mannose, or talose; the sugars belonging to the aminopentose or aminohexose series can be, for example, galactosamine, glucosamine or mannosamine; the sugars belonging to the deoxypentose or deoxyhexose series can be fucose or rhamnose; the sugars belonging to the disaccharide and oligosaccharide series can be for example cellobiose, lactose, maltose, melibiose, palatinose, sucrose, trehalose, turanose, maltotriose and maltotetraose; the hydrogenated forms of the above sugars can be erythritol, threitol, arabinitol, ribitol, xylitol, altritol, galactitol, glucitol, gulitol, iditol, mannitol, galactamine and glucamine, or the polyols belonging to the cyclic hexitol series, for example myoinositol.

These radicals derived from sugar can be in the form of D or L.

When Y or Z represents OM with M an organic or inorganic cation, this inorganic cation can be chosen from among >$NH_4^+$ and metals, particularly pharmaceutically acceptable metals, for example cations $Li^+$, $Na^+$, $K^+$, $Mg^{2+}$ and $Ca^{2+}$; the organic cations are particularly quaternary ammonia cations and cations derived from cyclic organic bases, for example triethylammonium, pyridinium, tetraethylammonium, tetrabutylammonium, cyclohexylammonium and dicyclohexylammonium cations.

When Z represents $X^2R^{17}$ with $R^{17}$ derived from a biologically active molecule, $R^{17}$ may be, for example, derived from a nucleoside such as thymidine, cytidine, adenosine or uridine, this last bearing, for example, an active substituent, a marker.

A non-restrictive list of examples of such substituents or elements is

— 3'-azido-3'deoxy-thymidine (AZT),

— 3'-difluoro-3'deoxy-thymidine,

— 2'-dideoxy,2'-fluoro-3-ara-adenosine,

— ribavirine, cordicepine, cytarabine, 2'-(methylamino)-5-deoxyuridine, psicofuranine, puromycine, thioguanosine, toyocamycine, trifluridine, tubercidine or vidarabine, all of these derivatives being known to chemists (cf Merck Index, 10th edition, 1983).

In the compounds of formula (Ia) or (Ib) described above, V and X represent O to advantage.

According to a suitable preparation method of the invention, one at least of Y and Z is —$X^1(CH_2)_aX^2(R^8)$, or

—$X^1(R^8)$

—$O(CH_2CH_2O)_pCH_3$ with p=6 to 100, or

—$O(CH(CH_3)CH_2O)_qCH_3$ with q=1 to 100.

The advantage of the presence of this type of substituents is that they are biologically well-accepted, and thus improve the biological compatibility of the compounds of the invention.

Preferably, when Y or Z is —$X^1R^8$, $X^1$ is —O—; when Y or Z is —$X^1(CH_2)_aX^2(R^8)$, $X^1$ and $X^2$ are —O— and a' is equal to 2.

For example, $R^8$ can be a radical derived from glucose, xylitol or mannose.

In the compounds of the invention corresponding to formula (Ia), the following radicals are preferably used for $R^1$:

$R_F$, $R_F$—W, and $R_F$—$(CH_2)_a$ W—A—$(CH_2)_b$, wherein
— $R_F$ is a radical of formula $C_nF_{2n+1}$ with n=6 to 8,
— W is the radical $(CH=CH)_d$—$(CH_2)_e$ with d=0 or 1; and e=0, 1, 2, 4 or 5,
— a is 0, 2, 4 or 5,
— A is —C(O)O— or —O—, and
— b is 1.

For $R^2$, the use of radicals of formula $R^1$ or a hydrogen atom is preferable.

In the compounds of the invention corresponding to formula (Ib), it is generally preferable to use for $R^2$ the radicals $R^1$ described above or hydrocarbon radicals of type $R_H$—A—$(CH_2)_b$ wherein $R_H$ is a linear alkyl radical of 1 to 22 carbon atoms, A is —O— or —C(O)O—, and b is equal to 1.

In these compounds, $R^3$ is preferably a radical of formula $R_F$—$(CH_2)_a$—W—A, $R_H$—A or $R_F$ with $R_F$ representing $C_nF_{2n+1}$, where n is an integer from 6 to 8, a is an integer from 4 to 10, A is —O— or —C(O)O—, and $R_H$ is a linear alkyl radical from 1 to 22 carbon atoms.

In compounds of formula (Ia) or (Ib), radicals of formula OH, OM, $X^2R^{17}$ or radicals with the same formula as Y are preferable for Z. As seen above, Y is preferably:

— $X^1(CH_2)_aX^2(R^8)$ or

— $X^1(R^8)$

— $O(CH_2CH_2O)_pCH_3$ with p=6 to 100, or —$O(CH(CH_3) CH_2O)_qCH_3$ with q=1 to 100.

The compounds of the invention of formula (Ia) or (Ib) can be prepared by the following steps, as illustrated in FIG. 1a:

1) Reaction of a compound of formula:

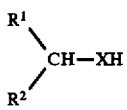   IIa or

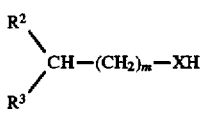   IIb wherein $R^1$, $R^2$, $R^3$, X and m have the above signification, with the compound of formula $VPCl_3$ wherein V has the above signification, to obtain a compound of formula:

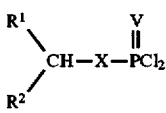   IIIa or

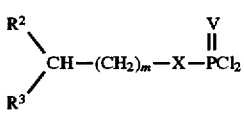   IIIb

2) Reaction of a compound of formula (IIIa) or (IIIb) with a compound of formula HY or HY' and a compound of formula HZ or HZ' wherein Y and Z have the signification given in claim 1 and Y' and Z' represent radicals Y and Z bearing hydroxyl groups protected by blocking groups, and 3) When a compound of formula HY' or HZ' is used, deprotection of the hydroxl groups of the compound of formula:

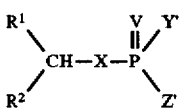   I'a or

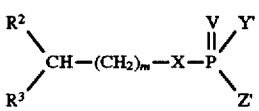   I'b thus obtained.

In the first step of this procedure, an alcohol, a thiol or a perfluoroalkylated amine is converted into a phosphorodichloridate or thiophosphorodichloridate by phosphorylation with phosphorus oxytrichloride or phosphorus thiotrichloride. This condensation can be achieved in a solvent such as ether, in the presence of triethylamine, with the drop-by-drop addition of the alcohol, thiol or amine solution in dry ether to a solution of $VPCl_3$ in ether to limit the reaction at the monoesterification stage. After elimination of excess $VPCl_3$, the phosphorodichloridate obtained generally contains less than 5% of diester and almost no triester, as this is undetectable.

In the second step of the procedure of the invention, the phosphodiester is prepared by condensation of HY or HY' with phosphorodichloridate, operating in an appropriate solvent such as chloroform, in the presence of triethylamine. During this reaction, the formation of the triester is difficult to avoid, and thus a mixture of the triester and the diester is obtained. The phosphodiester can, however, be separated from the mixture in the form of an ammonium salt, and then made to react with an appropriate reactive, HZ or HZ', which allows the introduction of group Z.

When group Y contains hydroxyl groups, the latter, with the exception of that on which the reaction takes place, must be protected by appropriate blocking groups. In this case, then, reactive HY' is used.

Some appropriate blocking groups are acetyl, benzyl, benzoyl, trityl, isopropylidene, benzylidene and cyclohexylidene groups.

The last step of the procedure consists in the deprotection of the hydroxyl groups of Y' to obtain the desired compound. This deprotection can be realized, for example in order to deacetyl, by treatment on a solution of sodium methylate. When it concerns phosphodiester, a compound of formula (Ia) or (Ib), wherein Z is ONa, is obtained.

In a variant of the procedure of the invention, after the first step of preparation of the phosphorodichloridate, a complementary step of transformation of this phosphorodichloridate into phosphoroditriaxolide by reaction with a triazole is performed. This allows the limitation, in the following step, of the formation of the phosphotriester.

Thus, when in the following step a molar ratio of HY'/phosphoroditriazolide of 0.5/1 is used, only traces of triester are obtained.

FIG. 1a (annexed) shows these two synthetic paths used in the invention.

Figure 1B:
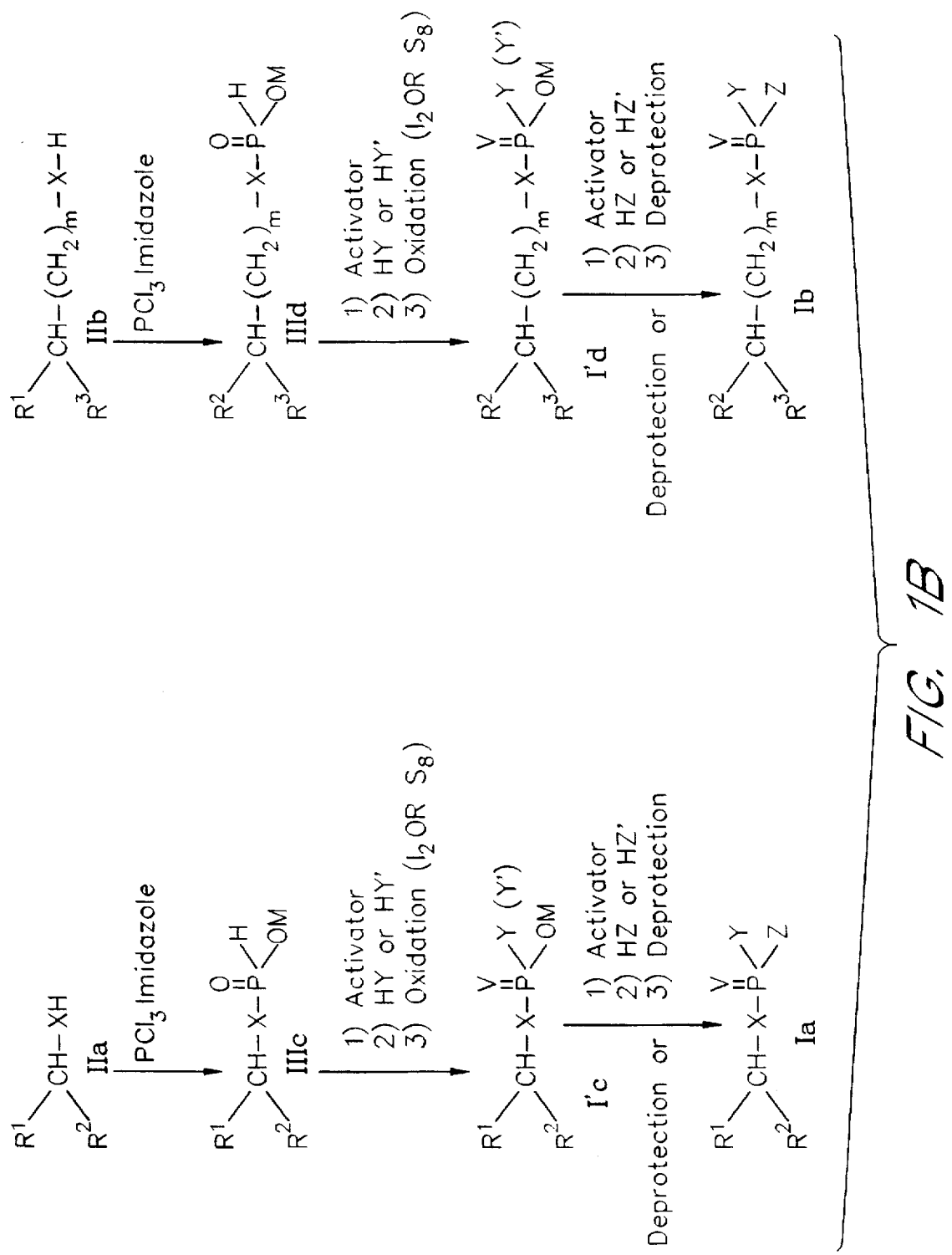
FIG. 1b sets forth a general synthetic scheme (Method 2) for the preparation of compounds having the general formula Ia and Ib.

Compounds of general formula (Ia) or (Ib) may also be prepared as shown in FIG. 1b, through a procedure including the following steps:

1) Reaction between, respectively, a compound of formula (IIa) or (IIb) and phosphoryltrichloride ($PCl_3$) in the presence of imidazole followed by hydrolysis, leading to a phosphonate compound of formula:

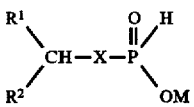   IIIc or

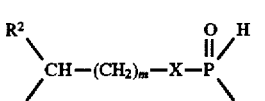   IIId wherein M is defined as given above;

2) Reaction respectively between a compound of formula (IIIc) or (IIId) and an activator (for example pivaloyl chloride, dicyclohexylcarbodiimide, trichloroacetonitrile or arylsulfonyl chloride or arysulfonyl diimidazolide), a compound of formula HY or HY', wherein Y and Y' are defined as above, leading, after oxidation by $I_2$ or $S_8$, to a compound of formula (I'c) or (I'd):

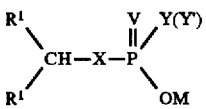   I'c or

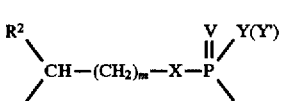   I'd

3) Reaction between a compound of formula (I'c) or (I'd), an activator as before, and a compound of formula HZ or HZ', wherein Z and Z' are defined above, followed by a deprotection in the case where a compound of formula HY' or HZ' is used.

The starting products used for this synthesis can be prepared by classical procedures or are available commercially.

The fluorinated derivatives of the invention are of considerable interest for numerous applications because they are strongly amphiphilic. They are, in particular, powerful surfactants, generally soluble or dispersible in water, biocompatible, for example without any detectable hemolytic action on human red blood cells, sometimes even at concentrations higher than 50 g/L. Moreover, active principles, particularly medicinal drugs, or an element or fragment that can serve as a marker, can be fixed to them by a chemical bond.

The present invention also concerns preparations for biomedical use containing at least one compound of formula (Ia) or (Ib) of the invention. These preparations can be in the form of solutions, micelles, dispersions, gels, emulsions and microemulsions in water or any other appropriate solvent. In these preparations, the fluorinated derivative of the invention can play the part of surfactant or cosurfactant, or of dispersant, or serve as a vehicle to solubilize or disperse an active principal in the preparation.

The compounds of the invention can also be used in the pharmaceutical field to prepare medicaments by using them as solvents, dispersants or emulsifiers, in solutions or administrable emulsions, for example for oral administration or by injection.

They can also be used as surfactants in preparations for pharmaceutical, veterinary or phytosanitary use, in preparations for use in biological and medical engineering, comprising in particular fluorocarbon-type oxygen carriers destined, among other uses, to be blood substitutes, or more generally to administer oxygen in vivo, or as fluorocarbon-type contrast agents containing a radiopaque element such as perfluoroctyl bromide (PFOB).

The compounds of the invention wherein Z is $X^2R^{17}$ can also be used as drugs or as markers, for example in preparations where these compounds serve to transport a pharmaceutical compound to an organ, a cell or a lesion, or to facilitate diagnosis, in particular by radiography, sonography or nuclear magnetic resonance imagery. Indeed, when $R^{17}$ bears an appropriate marker (fluorescein, a radiopaque or radioactive marker, etc.), the preparations can serve as contrast agents or markers. Being very powerful surfactants, the compounds of the invention can be used in emulsions.

Thus, the invention also concerns an emulsion comprising an oily phase, an aqueous phase and a surfactant constituted by a compound of the invention.

In an emulsion of this type, other surfactants such as lecithins and alkylene oxide copolymers, generally polyoxyethylene and polyoxypropylene can also be included.

In these emulsions, the oily phase can be a hydrocarbon or, preferably, a fluorocarbon or a highly fluorinated compound which can, for example, serve as a carrier of a gas such as oxygen. Fluorocarbons and highly fluorinated compounds can be, for example, linear or cyclic, with molecular weights preferably between 400 and 700, chosen from among the following compounds: bis-1,2-(F-alkyl)ethenes, particularly bis-1,2-(F-butyl)ethene (F-44E), 1-F-isopropyl-2-F-hexyl)ethene and bis-1,2-(F-hexyl)ethene, perfluorodecalin (F-decalin), perfluoromethyldecalins, perfluorodimethyldecalins, perfluoromethyl- and dimethyladamantanes, perfluorodi- and trimethylbicyclo(3,3,1)nonanes and their homologues, ethers of formulae: $(CF_3)_2CFO(CF_2CF_2)_2OCF(CF_3)_2$, $(CF_3)_2CFO(CF_2CF_2)_3OCF(CF_3)_2$, $(CF_3)_2CFO(CF_2CF_2)_2F$, $(CF_3)_2CFO(CF_2CF_2)_3F$, $F(CF(CF_3)CF_2O)_2CHFCF_3$, $F(CF(CF_3)CF_2O)_3CHFCF_3$, $(C_6F_{13})_2O$, $(C_4F_9)_2O$, amines $N(C_3F_7)_3$, $N(C_4F_9)_3$, perfluoromethylquinolidines and perfluoromethylisoquinolidines, halogen derivatives $C_6F_{13}Br$, $C_8F_{17}Br$ (PFOB), $C_6F_{13}CBr_2CH_2Br$, 1-bromo 4-perfluoroisopropyl cyclohexane, $C_8F_{16}Br_2$.

These highly fluorinated compounds can be used alone or in mixtures.

When the oily phase is a fluorocarbon or a highly fluorinated compound, it can represent from 10 to 125% weight/volume of the emulsion.

Generally, the content of the compound of the invention of these emulsions is from 0.01 to 30% in weight/volume when used alone or in association with another surfactant.

The aqueous phase may contain other additives, including inorganic salts, generally in the form of buffers, in order to adjust the pH and the oncotic and osmotic pressures, and to obtain an injectable isotonic composition.

In the preparations comprising the compounds of the invention, the latter can also be incorporated in other dispersed systems, particularly in liposomes.

Thus, the compounds of the invention are also useful in the preparation or modification of lipidic membranes, of liposomes or of niosomes which in turn are usable as drugs or vectors of drugs, also comprising oxygen carriers such as hemoglobin or modified hemoglobin or synthetic chelates. Virtually any active agent (also termed "bioactive agent") can be entrapped within the liposomes for use according to the present invention. Such agents include, but are not limited to, antibacterial compounds such as gentamicin, antiviral compounds such as rifampacin, antifungal compounds such as candicidin anti-parasitic compounds such as antimony derivatives, antineoplastic compounds such as vinblastine, vincristine, mitomycin C, doxorubicin, daunomycin, methotrexate, and cisplatin, among others, proteins such as albumin, toxins such as diptheria toxin, enzymes such as catalase, hormones such as growth hormone, neurotransmitters such as acetylcholine, lipoproteins such as alpha-lipoprotein, glycoproteins such as hyaluronic acid, immunoglobulins such as IgG, immunomodulators such as the interferons or the interleukins, dyes such as Arsenazo III, radiolabels such as $^{14}C$, radio-opaque compounds such as $^{99}Te$ fluorescent compounds such as carboxy fluoroscein, polysaccharides such as glycogen, cell receptor binding molecules such as estrogen receptor protein, nonsteroidal anti-inflammatories such as indomethacin, salicylic acid acetate, ibuprofen, sulindac, piroxicam, and naproxen; antiglaucomic agents such as timolol or pilocarpine, anesthetics such as dibucaine, nucleic acids such as thymine, polynucleotides such as RNA polymers. Also included are various bioactive chemical entities such as peptides, hormones, toxins, enzymes, neuotransmitters, lipoproteins, glycoproteins, immunomodulators, immunoglobulins, polysaccharides, cell receptor binding molecules, nucleic acids, polynucleotides, and the like. Liposomes can also be used in the field of contrast agents and cosmetics.

The procedures for preparing these lipidic membranes, these liposomes or these niosomes are well known to specialists in the field and comprise techniques using solvents, injection, ultrasounds or high-pressure mechanical homogenizers such as a Gaulin homogenizer or a microfluidizer.

Thus, in the present text, the term "dispersed system" may designate dispersions, emulsions, liposomes, niosomes, vesicles, gels, micellar solutions, microemulsions or other phases of similar structure, containing polar or non-polar substances, including drugs, or an oil, which can be hydrogenated or not and which can contain one or several other surfactants.

In the preparations comprising liposomes, these can be formed from natural or synthetic phospholipids or lecithins, for example perfluoroalkylated lecithins, or from a mixture of phospholipids and steroids such as cholesterol. In these preparations based on liposomes, the compounds of the invention can be incorporated in a liposomal vehicle and the liposomes can be polymerized.

The preparations, solution, gels, emulsions, dispersions, liposomes and microemulsions of the invention can be used in human and veterinary medicine and in biology, in particular as blood substitutes, contrast agents for diagnosis, media for the treatment of cerebral and cardiac ischemia for perioperative hemodilution, for the preservation of organs, tissues, embryos, or semen, media for therapeutic and cardiovascular surgery, for example as cardioplegic or reperfusion solutions, in coronary angioplasty or as adjuvants in cancer radio- and chemotherapy, and as vectors of medicaments or bioactive agents.

Figure 2:
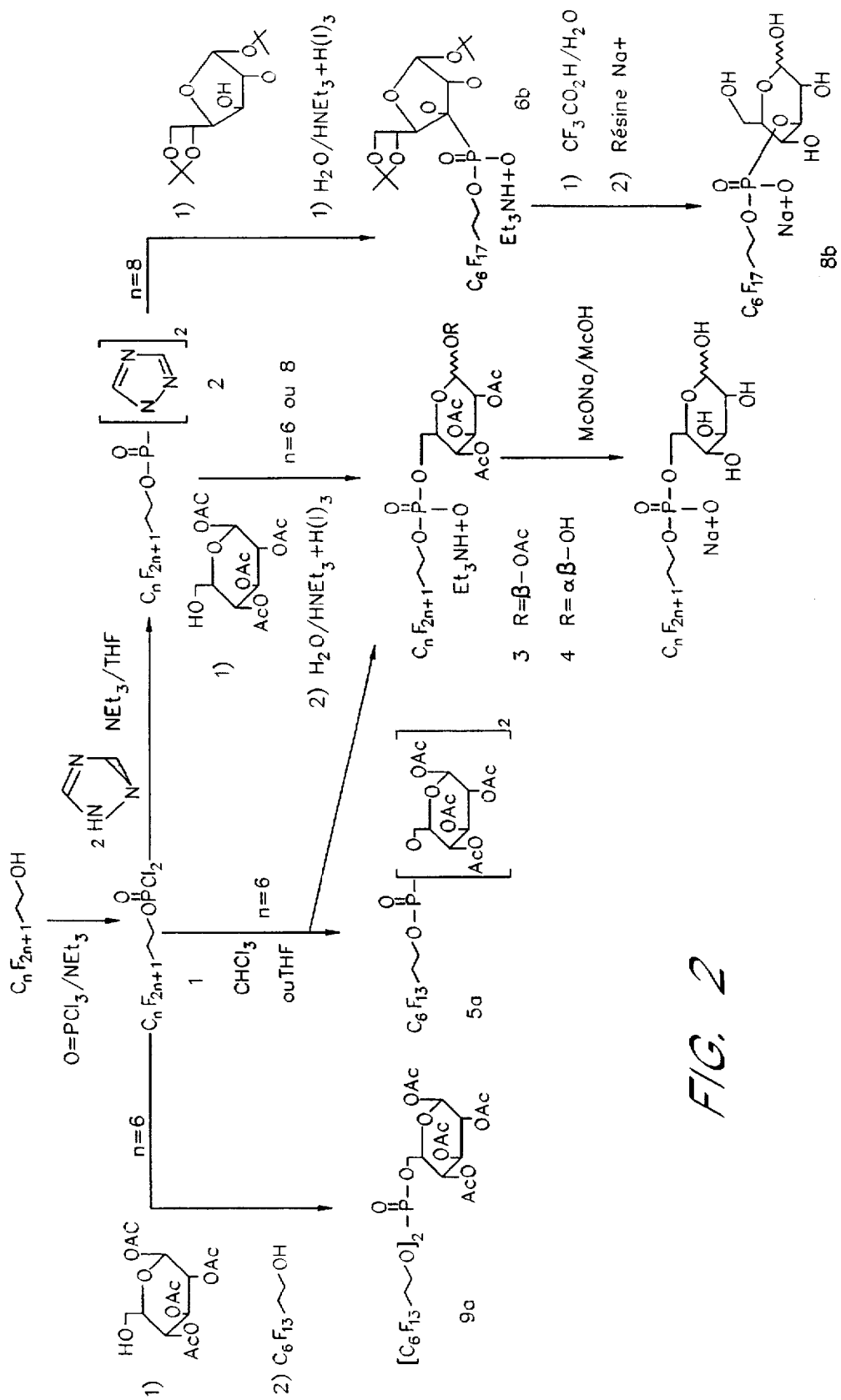
FIG. 2 sets forth a synthetic scheme for the preparation of compounds 3 to 9.
Figure 3A:
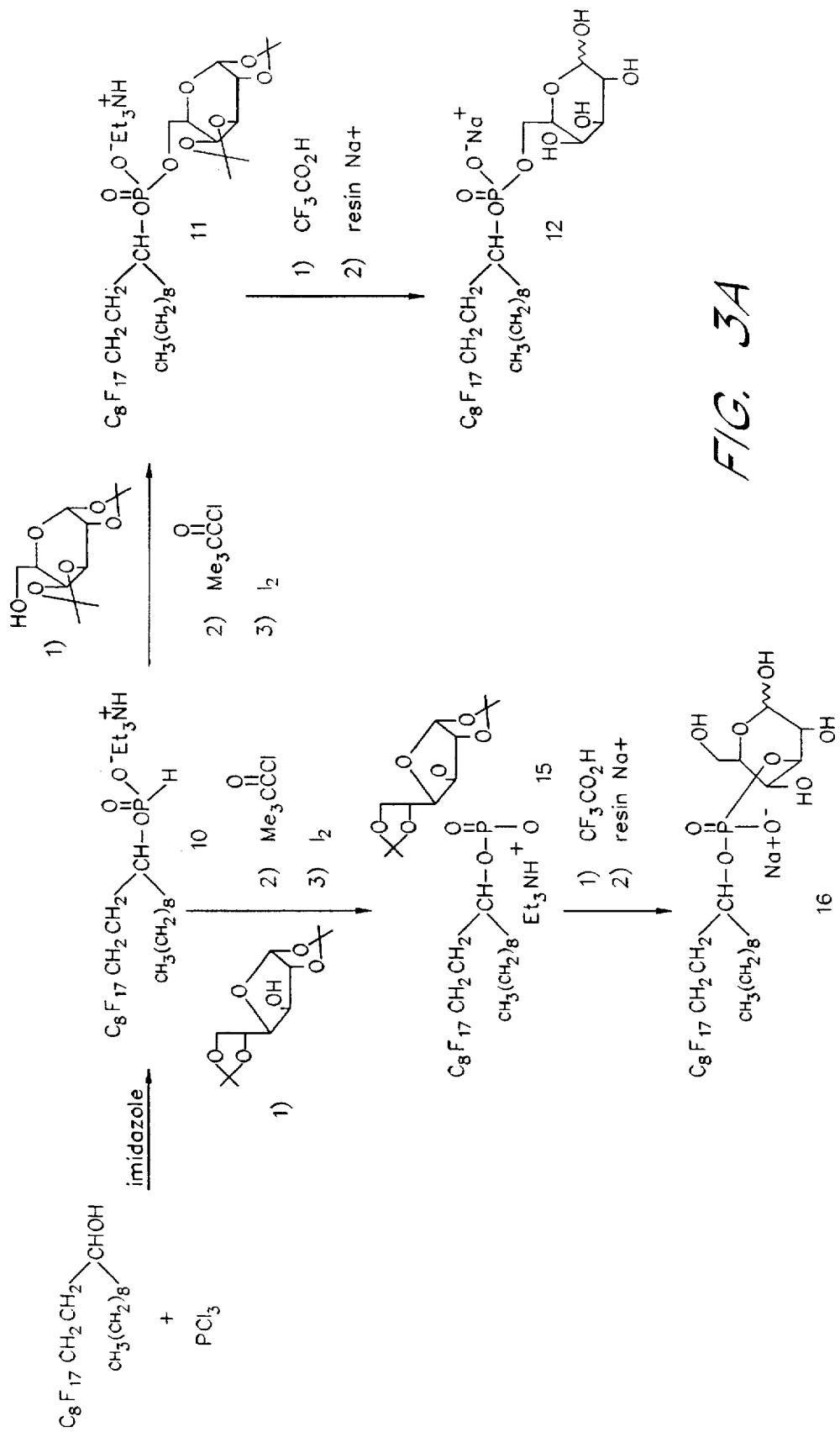
FIG. 3a sets forth a synthetic scheme for the preparation of compounds 10–12, 15, and 16.
Figure 3B:
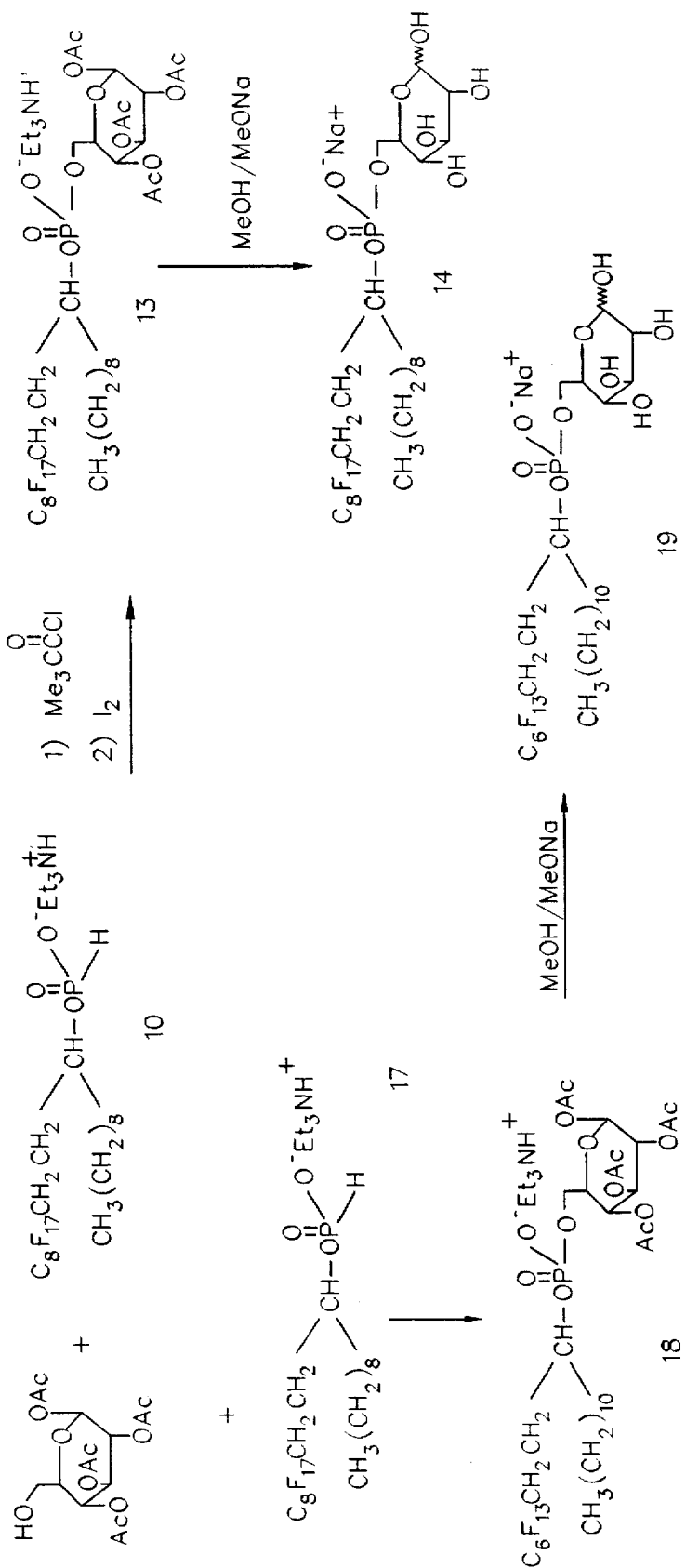
FIG. 3b sets forth a synthetic scheme for the preparation of compounds 13, 14, and 17–19.
Figure 4:
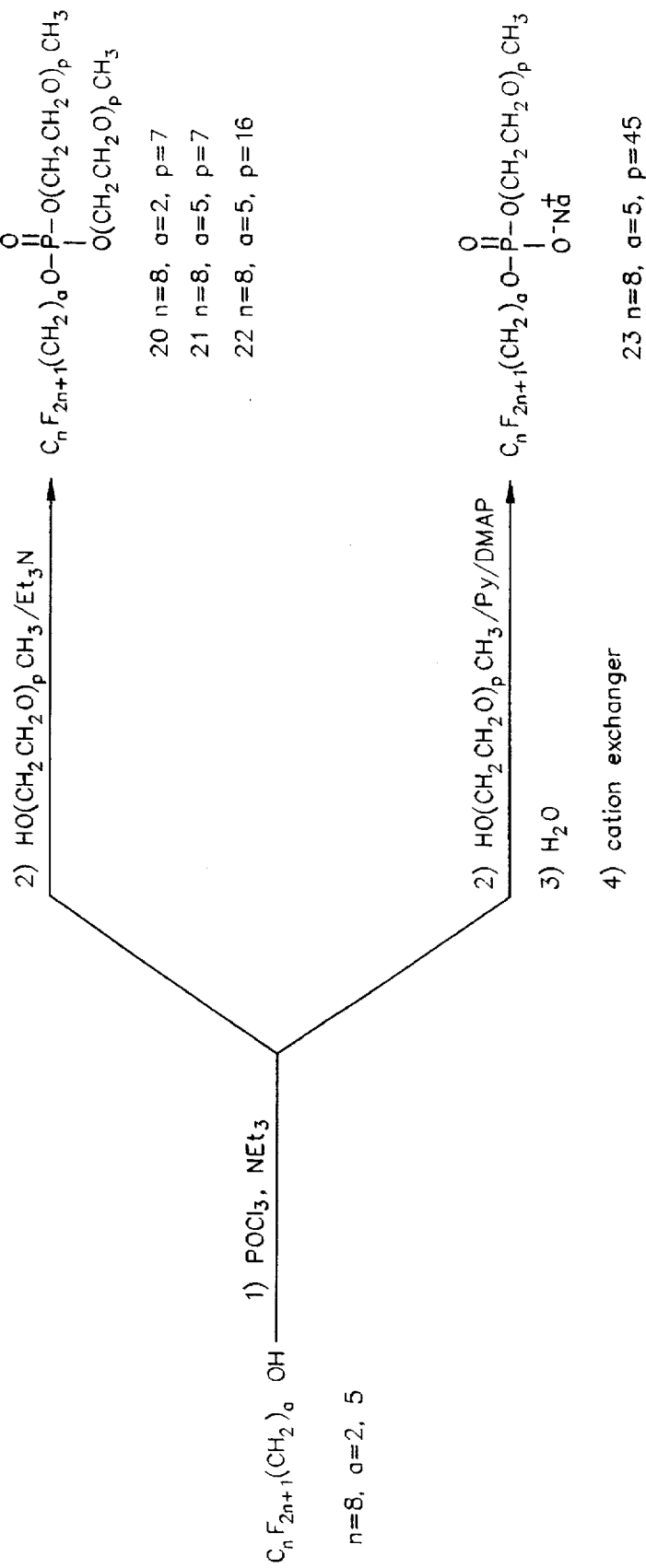
FIG. 4 sets forth a synthetic scheme for the preparation of compounds 20 to 23.
Figure 5:
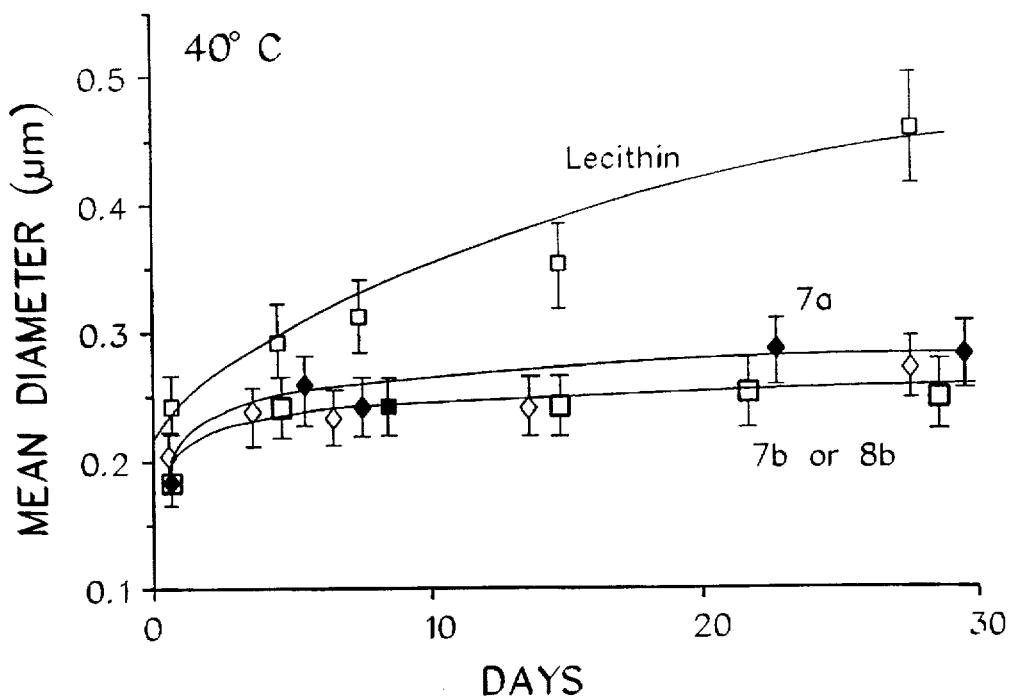
FIG. 5 demonstrates the ageing at 40° C. of perfluorodecalin(PFD) (50% w/v) sterilized emulsions prepared with 3% of surfactant: lecithin, 7a, 7b, or 8b. (Curves of 7b and 8b are superimposable.)
Figure 6:
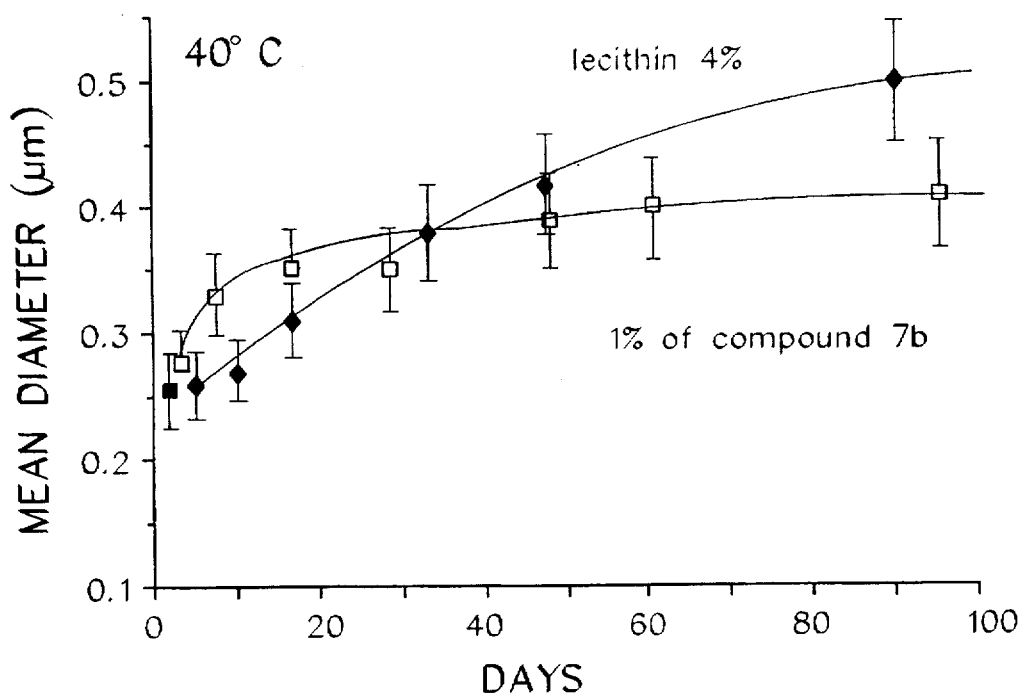
FIG. 6 demonstrates the ageing at 40° C. of perfluorooctyl bromide(PFOB) (90% w/v) sterilized emulsions prepared with 4% of lecithin or 1% of compound 7b.
Figure 7:
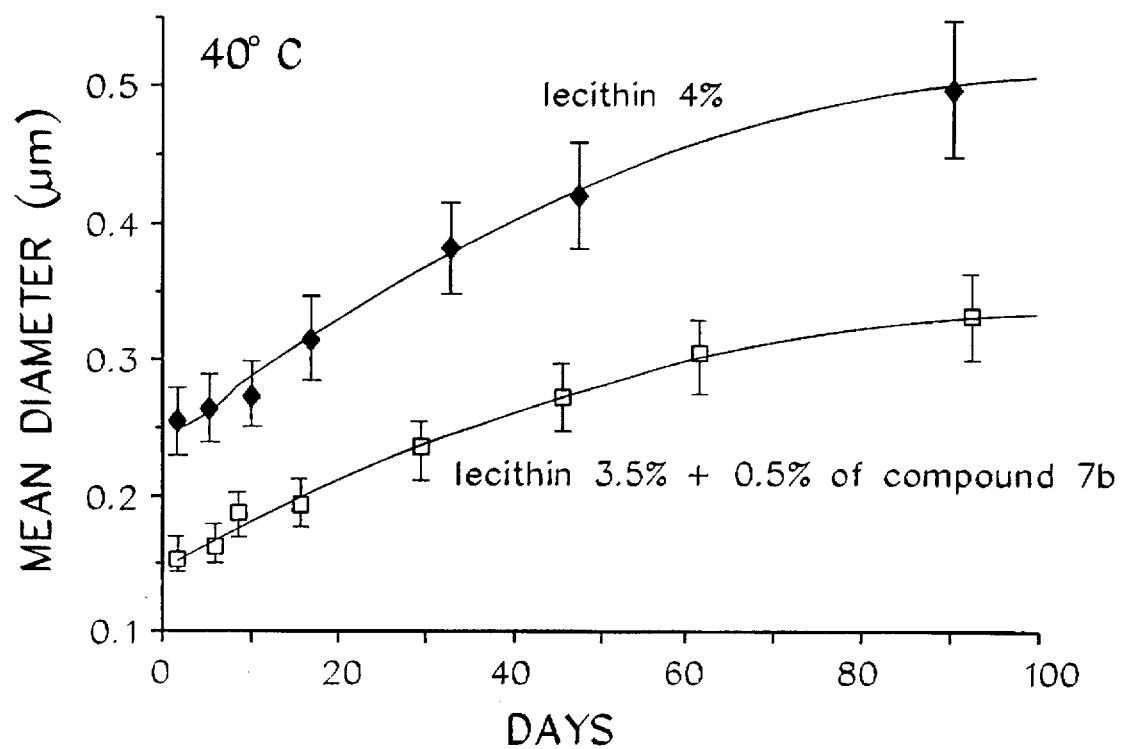
FIG. 7 demonstrates the ageing at 40° C. of PFOB (90% w/v) sterilized emulsions prepared with 4% of lecithin or with lecithin 3.5/0.5% w/v respectively.

Other characteristics and advantages of the invention will be better seen on reading the following examples, which are of course non-restrictive but given as illustrations with reference to the attached drawing, wherein:

FIG. 1, already mentioned, represents schematically four synthetic paths for the compounds of the invention, FIGS. 2, 3 and 4 represent the synthetic schemes corresponding to the examples described, FIGS. 5, 6 and 7 represent the evolution of the average dimensions (in μm) of particles of sterilized emulsions prepared in conformity with the invention as a function of time (in days), during trials of ageing realized at 40° C.

FIG. 5 concerns emulsions containing 50% w/v of perfluorodecalin (FDC) and 3% w/v of the compound 7a, 7b or 8b; the results with 7b and 8b are merged.

In FIG. 5, the results obtained in the same conditions with a 50% w/v FDC, 3% w/v lecithin emulsion are shown for comparison.

FIGS. 6 and 7 show, for comparison, the results obtained with an emulsion containing 90% w/v of perfluoroctyl bromide (PFOB) and 4% w/v of lecithin.

The present invention is described below in detail using the following examples, but the chemical reactions described are disclosed in terms of their general application to the preparation of the amphiphilic molecules of the invention. Occasionally, the reaction may not be applicable as described to each compound included within the disclosed scope of the invention. The compounds for which this occurs will be readily recognized by those skilled in the art. In all such cases, either the reactions can be successfully performed by conventional modifications known to those skilled in the art, e.g. by appropriate protection of interfering groups, by changing to alternative conventional reagents, or by routine modification of reaction conditions. Alternatively, other reactions disclosed herein or otherwise conventional will be applicable to the preparation of the corresponding compounds of the invention. In all preparative methods, all starting materials are known or readily preparable from known starting materials; all temperatures are set forth uncorrected in degrees Celsius; and, unless otherwise indicated, all parts and percentages are by weight.

It is believed that one skilled in the art can, using the preceding description, utilize the invention to its fullest extent. The following preferred embodiments are, therefore, to be construed as merely illustrative and not limitative for the remainder of the disclosure in any way whatsoever.

EXAMPLES 1 TO 3:

[2-(F-Hexyl)ethyl](1,2,3,4-tetra-O-acetyl-β-D-glucopyranosyl) (Triethylammonium) Phosphate 3a; [2-(F-Hexyl)ethyl] 6-O-(2,3,4-Tri-O-acetyl-D-glucopyranosyl) (Triethylammonium) Phosphate 4a; [2-(F-Hexyl)ethyl] [Di-(1,2,3,4-tetra-O-acetyl-β-D-glucopyranosyl)] Phosphate 5a Pathway 1: Phosphorylation of 1,2,3,4-tetra-O-acetyl-β-D-glucopyranose by 1a.

30.6 g of 2-(F-hexyl)ethanol and 17.0 g of triethylamine in ether were allowed to react with 15.4 g of phosphorus oxychloride at 0° C. to give 38.7 g of 2-(F-hexyl) ethyl phosphorodichloridate 1a (96%).

3.0 g of 1,2,3,4-tetra-O-acetyl-β-D-glucopyranose and 1.7 g of triethylamine in chloroform were added to 4.1 g of 1a in chloroform. Treatment and silica gel column chromatography gave solid 5a (2.6 g, 55%) and 2.9 g of a mixture in a 95/5 ratio composed of 3a and 4a (ethylammonium salt). Trituration with ether yielded pure solid 3a (2.0 g, 26%).

Pathway 2: Phosphorylation of 1,2,3,4-tetra-O-acetyl-β-D-glucopyranose by 2a.

3.7 g of 1H-1,2,4-triazole and 5.5 g of triethylamine were allowed to react with 13.0 g of 1a in tetrahydrofuran. 4.7 g of 1,2,3,4-tetra-O-acetyl-β-D-glucopyranose in pyridine were added to the solution of 2a. After treatment and filtration through a silica gel column, 10.0 g of a 3a/4a mixture in a 95/5 ratio were obtained. Trituration with ether yielded 3a (7.6 g, 65%).

Analysis of 3a: $[\alpha]_D$ +12.7° (c 1.0, chloroform); $^{31}$P-n.m.r. (CDCl$_3$): δ −0.18;

Analysis of 4a: $[\alpha]_D$ +29.0° (c 0.9, chloroform); $^{31}$P-n.m.r. (CDCl$_3$): δ −0.41.

Analysis of 5a: $[\alpha]_D$ +14.8° (c 1.2, chloroform); $^{31}$P-n.m.r. (CDCl$_3$): δ −1.40.

EXAMPLE 4:

[2-(F-Hexyl)ethyl](6-D-glucosyl)(sodium) phosphate 7a

Compound 3a (5.4 g) was stirred in 1% methanolic sodium methoxide. The solution was brought to pH 4 with an Amberlite IR-120 resin (H$^+$ form), then passed through an Amberlite IR-120 resin column (Na$^+$ form). The resulting solid dissolved in methanol was precipitated by addition of ether to provide solid 7a (3.7 g, 93%).

Analysis of 7a: $[\alpha]_D$ +14.8° (c 1.2, water); $^{31}$P-n.m.r (CD$_3$OD): δ 2.09 and 2.06; Anal. Calc. for C$_{14}$H$_{15}$F$_{13}$NaO$_9$P.H$_2$O (646.2): C, 26.02; H, 2.65; F, 38.22; Na, 3.55; P, 4.79. Found: C, 26.39; H, 2.71; F, 38.70; Na, 3.73; P, 4.80.

EXAMPLES 5 AND 6:

[2-(F-Octyl)ethyl] (1,2,3,4-Tetra-O-acetyl-β-D-glucopyranosyl)(Triethylammonium) Phosphate 3b; [2-(F-Octyl)ethyl] 6-O-(2,3,4-Tri-O-acetyl-D-glucopyranosyl) (Triethylammonium) Phosphate 4b 13.8 g of 1,2,3,4-tetra-O-acetyl-β-D-glucopyranose in pyridine was added to 2b in tetrahydrofuran prepared as above from 1H-1,2,4-triazole (10.9 g), 1b (45.9 g) and triethylamine (16 g). Similar treatment as above gave 32 g of a 3b/4b mixture (95/5 ratio). Solid 3b (24.9 g, 64%) was obtained after trituration with ether.

Analysis of 3b: $[\alpha]_D$ +11.0° (c 1.0, chloroform); $^{31}$P-n.m.r. (CDCl$_3$): δ −0.11.

EXAMPLE 7:

[2-(F-Octyl)ethyl](6-D-glucosyl)(sodium) phosphate 7b

After processing as described for 3a, compound 3b (24 g) yielded white solid 7b (16.9 g, 92%). O-Deacetylation of a 3b/4b mixture (1.0 g), as described above, gave also pure 7b (0.7 g, 76%).

Analysis of 7b: $[\alpha]_D$ +11.8° (c 1.0, water); $^{31}$P-n.m.r. (CD$_3$OD): δ 2.13 and 2.17; Anal. Calc. for C$_{16}$H$_{15}$F$_{17}$NaO$_9$P.H$_2$O (746.2): C, 25.75; H, 2.29; F, 43.28; Na, 3.08; P, 4.15. Found: C, 25.96; H, 2.15; F, 44.18; Na, 3.00; P, 4.19.

EXAMPLE 8:

[2-(F-Octyl)ethyl] (1,2:5,6-Di-O-isopropylidene-α-D-glucofuranosyl) (Triethylammonium) Phosphate 6b

6.4 g of 1,2:5,6-di-O-isopropylidene-α-D-glucofuranose in pyridine were added to 2b prepared from 1H-1,2,4-triazole (6.8 g), 1b (28.8 g) and triethylamine (10 g). After treatment and chromatography, 3.2 g of unreacted sugar (50%) was recovered by elution with ether, then elution with chloroform/methanol (80/20) yielded 10.9 g of 6b (triethylammonium salt).

Analysis of 6b: $[\alpha]_D$ −17.9° (c 1.2, chloroform); $^{31}$P-n.m.r. (CD$_2$Cl$_2$): δ −1.24.

EXAMPLE 9:

[2-(F-Octyl)ethyl] (3-D-Glucosyl) (Sodium) Phosphate 8b

6b (8.8 g, 10 mmol) was dissolved in 90% (v/v) aqueous trifluoroacetic acid. After treatment, the resulting solid dissolved in a water-methanol mixture was passed through an Amberlite IR-120 resin column (Na$^+$ form). Lyophilisation of the appropriated fractions led to solid 8b (4.6 g, 65%).

Analysis of 8b: $[\alpha]_D$ +14.4° (c 1.1, water); $^{31}$P-n.m.r. (CD$_3$OD): δ 2.82 et 2.66; Anal. Calc. for C$_{16}$H$_{15}$F$_{17}$NaO$_9$P.H$_2$O (746.2): C, 25.75; H, 2.29; F, 43.28; Na, 3.08; P, 4.15. Found: C, 26.20; H, 2.05; F, 43.18; Na, 3.08; P, 4.13.

EXAMPLE 10:

bis-[2-(F-Hexyl)ethyl] 6-(1,2,3,4-Tetra-O-acetyl-β-D-glucopyranosyl) Phosphate 9a

4.23 g of 1a were reacted in tetrahydrofuran with 3.06 g of 1,2,3,4-tetra-O-acetyl-β-D-glucopyranose for 19 h, then 3.84 g of 2-(F-hexyl)ethanol were added. After 27 h of reaction, purification by chromatography led to 4.04 g (41%) of 9a.

Analysis of 9a: $[\alpha]_D$ +8.0° (c 1.1, chloroform); $^{31}$P-n.m.r. (CDCl$_3$): −1.58.

EXAMPLE 11:

{1-[2-(F-Octyl)ethyl]decyl} (Triethylammonium) Hydrogenphosphonate 10

To a solution of imidazole (3.88 g) in toluene at 0° C. was added dropwise PCl$_3$ (1.52 mL) followed by triethylamine (8.4 mL). After 15 min of stirring, 1-[2-(F-octyl)ethyl] decanol (2.42 g) in toluene was added dropwise. After 90 min, the reaction mixture was quenched with M.TEAB then concentrated. Methylene chloride was added and the organic layer was washed with water and M.TEAB, dried, concentrated and purified on silica gel. Appropriate fractions treated with M TEAB then concentrated yielded 10 (2.11 g, 70%).

Analysis of 10: $^{31}$P-n.m.r. (CDCl$_3$): δ 3.5.

EXAMPLE 12:

{1-[2-(F-Octyl)ethyl]decyl}(1,2:3,4-di-O-isopropylidene-α-D-galactopyranosyl) (Triethylammonium) Phosphate 11

A mixture of 10 (5.91 g) and 1,2:3,4-di-O-isopropylidene-α-D-galactopyranose (2 g) dissolved in pyridine reacted with pivaloyl chloride (2.37 mL). After 15 min, iodide (3.89 g) in pyridine/water (98/2, 19.1 mL) was added. After 4 hours of stirring, the solution was evaporated, then methylene chloride was added and the organic layer was washed with M Na$_2$S$_2$O$_3$, water and M TEAB, dried, concentrated and purified on a silica gel. Treatment with M TEAB yielded 11 (3.91 g, 50%).

Analysis of 11: $^{19}$F-n.m.r. (CDCl$_3$): δ −81.5 (CF$_3$), −115 (CF$_2$CH$_2$), −122.6-123.8 (10F), −126.8 (C$\underline{F}_2$CF$_3$).

EXAMPLE 13:

{1-[2-(F-Octyl)ethyl]decyl} (6-D-Galactosyl) (Sodium) Phosphate 12

11 (2.9 g, acid form) was stirred in CF$_3$CO$_2$H—H$_2$O (90/10). After 15 min, the solvent was evaporated. The resultant oil dissolved in aqueous methanol was treated with an Amberlite IR-120 resin (Na$^+$ form). Filtration, concentration and precipitation in acetone led to a solid which was purified by trituration with ether to give solid 12 (1.7 g, 70%).

Analysis of 12: $^{13}$C-n.m.r. (CD$_3$OD): δ 100.8 (C-1b), 94.2 (C-1a), 75.4 (d $^3J_{C,P}$ 6.1 Hz, C-5β), 74 (d, $^3J_{C,P}$ 7.3 Hz, CH), 73.7 (C-3β), 72.7 (C-2β), 69.8 (C-5a), 69.4 (C-4a), 69.3 (C-3a), 69.2 (C-4β), 68.6 (C-2a), 64.3 (2d, $^2J_{C,P}$ 5.5 Hz, C-6a, C-6β), 36.3 (d, $^3J_{C,P}$ 5.5 Hz, C-1), 33.1 (C-2), 30.6 (2s, (CH$_2$)$_4$), 28 (t, $^2J_{C,F}$ 22 Hz, CH$_2$C$_8$F$_{17}$), 26.7 (CH$_2$CH$_2$C$_8$F$_{17}$), 26.1 (C-7), 23.7 (C-8), 14.4 (C-9); $^{31}$P-n.m.r. (CD$_3$OD): δ 1.4.

EXAMPLE 14:

{1-[2-(F-Octyl)ethyl]decyl}(1,2,3,4-Tetra-O-acetyl-β-D-glucopyranosyl) (Triethylammonium) Phosphate 13

{1-[2-F-octyl)ethyl]decyl} (triethylammonium) hydrogenphosphonate 10 (2.58 g) and 1,2,3,4-tetra-O-acetyl-β-D-glucopyranose (1.17 g) in pyridine reacted with pivaloyl chloride (0.93 mL) and iodine (1.7 g) in pyridine/water (98/2) according to the method described for 11 yielded 13 (1.37 g, 36%).

Analysis of 13: $^{31}$P-n.m.r. (CDCl$_3$): δ −0.45.

EXAMPLE 15:

{1-[2-(F-Octyl)ethyl]decyl} (6-D-Glucosyl) (Sodium) Phosphate 14

13 (0.73 g) was stirred for 15 min in 1% methanolic sodium methoxide. The solution was brought to pH 4 with an Amberlite IR-120 resin (H$^+$ form) then treated with an Amberlite IR-120 resin (Na$^+$ form). Concentration and precipitation in acetone led to a solid purified by trituration with ether giving 14 (0.39 g, 70%).

Analysis of 14: $^{31}$P-n.m.r. (CD$_3$OD): δ 2.2.

EXAMPLE 16:

{1-[2-(F-Octyl)ethyl]decyl}(1,2:5,6-Di-O-isopropylidene-α-D-glucofuranosyl) (Triethylammonium) Phosphate 15

10 (4 g, 5.2 mmol) reacted with 1,2:5,6-di-O-isopropylidene-α-D-glucofuranose (1.35 g) according to the method described for 11 yielded 15 (4.3 g, 81%).

Analysis of 15: IR (cm$^{-1}$): 3445 (N—C$_2$H$_5$), 2930-2860 (CH), 1210-1150 (CF), 1210 (P=O), 1075 (P—O—C).

EXAMPLE 17:

{1-[2-(F-Octyl)ethyl]decyl} (3-D-Glucosyl) (Sodium) Phosphate 16

15 (4.2 g, 4.84 mmol) treated with the same process as for the compound 11 yielded 16 as a solid (1.78 g, 50%).

Analysis of 16: $^{31}$P-n.m.r. (CD$_3$OD): δ 3.2 and 2.8.

EXAMPLE 18:

{1-[2-(F-Hexyl)ethyl]dodecyl} (Triethylammonium) Hydrogenphosphonate 17

As described for the compound 10, PCl$_3$ (1.88 mL) and [1-2-(F-hexyl)ethyl]dodecanol (3 g) yielded 17 (3.15 g, 80%).

Analysis of 17: $^{31}$P-n.m.r. (CDCl$_3$): δ 3.9.

EXAMPLE 19:

{1-[2-(F-Hexyl)ethyl]dodecyl} (1,2,3,4-Tetra-O-acetyl-β-D-glucopyranosyl) (Triethylammonium) Phosphate 18

Compound 17 (0.5 g) reacted with 1,2,3,4-tetra-O-acetyl-β-D-glucopyranose (0.26 g) as described for 11 yielding 18 (0.38 g, 50%).

EXAMPLE 20:

{1-[2-(F-Hexyl)ethyl]dodecyl} (6-D-Glucosyl) (Sodium) Phosphate 19

18 (3.5 g) treated as the compound 13 yielded a solid (1.6 g, 60%).

EXAMPLE 21:

[2-(F-Octyl)ethyl]bis [Polyethylene Glycol Methyl Ether] Phosphate Triester 20, n=7

2-(F-octyl)ethanol (7.9 g) and triethylamine (2.9 mL) reacted in ether at 0° C. with POCl$_3$ (1.90 mL). After filtration, the excess of POCl$_3$ was distilled. The crude product was dissolved in ether and polyethylene glycol methyl ether (23.0 g:MW 350) and triethylamine (9.3 mL) were added. After stirring at room temperature for 48 hours and treatment, 11.5 g (56%) of 20 were obtained.

Analysis of 20: $^1$H-n.m.r. (CDCl$_3$): δ 2.32–2.65 (m, 2H, CF$_2$CH$_2$), 3.31 (s, 6H, OCH$_3$), 3.43–3.75 (m, ⁻ 57 H, CH$_2$O(CH$_2$CH$_2$O)$_{n-1}$), 4.07–4.23 (m, 4H, POCH$_2$), 4.31 (dt, 2H, $^3J_{HP}$=7.7 Hz, $^3J_{HH}$=5.9 Hz, CH$_2$OP); $^{31}$P-n.m.r. (CDCl$_3$): δ -0.69.

EXAMPLE 22:

[5-(F-Octyl)pentyl]bis [Polyethylene Glycol Methyl Ether] Phosphate Triester 21, n=7

The process of example 21 applied first to 5.0 g of 5-(F-octyl)pentanol, 1.7 mL of triethylamine and 1.1 mL of POCl$_3$, then to 12.8 g of polyethylene glycol methyl ether (MW 350) and 7.0 mL of triethylamine yielded, after treatment, 7.0 g (57%) of 21.

Analysis of 21: $^{31}$P-n.m.r. (CDCl$_3$): δ -0.26.

EXAMPLE 23:

[5-(F-Octyl)pentyl]bis [Polyethylene Glycol Methyl Ether] Phosphate Triester 22, n=16

The process of example 21 applied first to 4.8 g of 5-(F-octyl) pentanol, 1.6 mL of triethylamine and 1.1 mL of POCl$_3$, then to 25.7 g of polyethylene glycol methyl ether (MW 750) and 3.1 mL of triethylamine yielded, after treatment, 10.0 g (51%) of 22.

Analysis of 22: $^1$H-n.m.r. (CDCl$_3$): δ 1.31–1.72 (m, 6H, (CH$_2$)$_3$), 1.80–2.15 (m, 2H, CF$_2$CH$_2$), 3.28 (s, 6H, OCH$_3$), 3.40–3.80 (m, ⁻ 130 H, CH$_2$O(CH$_2$CH$_2$O)$_{n-1}$), 3.80–4.16 (m, 6H, CH$_2$OP and POCH$_2$); $^{31}$P-n.m.r. (CDCl$_3$): δ -0.19.

EXAMPLE 24:

[5-(F-Octyl)pentyl] [Polyethylene Glycol Methyl Ether] Phosphate, Sodium Salt 23, n=45

The process of example 21 for the first step was applied to 7.4 g of 5-(F-octyl)pentanol, 2.5 mL of triethylamine and 1.7 mL of POCl$_3$. After filtration and removal of the solvent, the crude reaction product was dissolved in chloroform and 29.4 g of polyethylene glycol methyl ether (MW 2000), 9.5 mL of pyridine and 0.2 g of dimethylaminopyridine were added. Stirring for 24 hours and treatment yielded 23 (21 g, 55%).

Analysis of 23: $^1$H-n.m.r. (CDCl$_3$): δ 1.26–1.70 (m, 6H, (CH$_2$)$_3$), 1.75–2.17 (m, 2H, CF$_2$CH$_2$), 3.30 (s, 3H, OCH$_3$), 3.34 (m, ⁻190 H, CH$_2$OP and CH$_2$O(CH$_2$CH$_2$O)$_{n-1}$), 3.93 (m, 2H, POCH$_2$); $^{31}$P-n.m.r. (CDCl$_3$): δ -3.50.

SURFACE ACTIVITY

The compounds described in this invention are very efficient surface agents, greatly lowering the surface ($\gamma_s$) and interfacial ($\gamma_i$) tensions between water and a fluorocarbon when added to water. Thus at 1 g/L in water, $\gamma_s$ goes from 73 (pure water) to 19.7–33.8 mNm$^{-1}$, and $\gamma_i$[water/perfluorodecalin (FDC) or perfluorooctyl bromide (PFOB)] goes from 56 and 51 (in the absence of surfactant) to 5.1–8.9 mNm$^{-1}$ and 4.7–10.5 mNm$^{-1}$ respectively, as illustrated by the examples assembled in the table below. These compounds are also characterized by low values of critical micellar concentration:

(CMC:from $1.10^{-6}$ to $1.7.10^{-3}$M).

| | | Surface Activity Data of Aqueous Solutions (20° C.; ± 0.3 mNm$^{-1}$). | | | | | | |
|---|---|---|---|---|---|---|---|---|
| Compound | MW | Dispersibility at 25° C., g/L in water | CMC (mM) | Concentration | | $\gamma_s$ | $\gamma_i$/FDC | $\gamma_i$/PFOB |
| H$_2$O | | | | | | 73.0 | 56.0 | 51.0 |
| 7a | 646.2 | 350 | 1.55 | 1 | 1.548 | 19.7 | 5.6 | 4.7 |
| 8b | 746.2 | 250 | 1.68 | 1 | 1.340 | 27.5 | 5.6 | 8.3 |
| 20 | 1208 | >100 | 0.025 | 0.1 | 0.083 | 33.8 | 13.1 | 9.2 |
| 21 | 1250 | >100 | 0.001 | 0.01 | 0.008 | 29.6 | 9.6 | 7.5 |

BIOLOGICAL EVALUATION

The biocompatibility of the compounds claimed in the present invention is illustrated in particular by the fact that aqueous solutions at 1 g/L of these compounds do not modify the growth and viability of Namalva cell cultures. The perfluoroalkylated chain of these compounds confers a protective character; thus a dispersion at 30 g/L of compound 7b in a solution at 20 g/L of Pluronic F-68® shows no hemolytic effect, whereas an aqueous solution of its hydrocarbon analogue is very hemolytic even at 5 g/L. Compound 7a shows no hemolytic activity, even at a concentration as high as 100 g/L. It is also characterized by a $LD_{50}$ on the order of 750 mg/kg in intravenous injection into mice. Compound 22 is non-hemolytic at a 50 g/L concentration, and its $LD_{50}$ is higher than 2000 mg/kg in intravenous injection into mice. Concerning compounds 21 and 22, which differ by the degree of polymerization of the polyethyleneglycol head, it should be pointed out that their in vivo tolerance increases from 21 to 22, i.e. with increasing degree of polymerization. Furthermore, these derivatives show a higher i.v. tolerance than the single-chain compounds disclosed in WO 90/15807 C ($25 \leq LD_{50} \leq 125$ mg/kg bw).

| | Cells Cultures | | Hemolysis | | Toxicity in Mice | |
|---|---|---|---|---|---|---|
| Product | Conc g/L | Growth/Viab | Conc* g/L | % hem. | Dose | Survival |
| 7a | 1 | 51/97 | 100 | 0 | 750 | 4/10 |
| | 0.1 | 82/97 | | | | |
| 7b | 1 | 76/104 | 30ª | 0 | 125 | 10/10 |
| 8a | 1 | 87/100 | | | 250 | 9/10 |
| 20 | | | 50 | 0 | | |
| 21 | | | 50 | 0 | 500 | 10/10 |
| | | | | | 1000 | 3/10 |
| 22 | | | 100 | 0 | 2000 | 10/10 | a dispersed in a 20 g/L Pluronic F-68 solution.
*solution added to an equal volume of a suspension, at 1% concentration of washed red blood cells in saline.

EMULSIONS

The products described in this invention, used as surfactants or co-surfactants, allow the preparation and stabilization of fluorocarbon emulsions. The emulsions were prepared by sonification (BRANSON B30 sonicator) (for 50% w/v of fluorocarbon) or by high-pressure microfluidization ((MICROFLUIDICS M 110)) (for more concentrated fluorocarbon emulsions). The ageing of these emulsions at 40° C. (accelerated ageing conditions) was followed by measuring the average size of the particles by a photosedimentation method (HORIBA CAPA 500) and compared with reference emulsions prepared with natural egg-yolk lecithins or poloxamers, for example Pluronic F-68.

Emulsions prepared with the sonicator

EXAMPLE 25:

Formulation with 7b 3% w/v; Perfluorodecalin (FDC) 50% w/v

To prepare 12 mL of an emulsion of FDC (50% w/v) with 3% w/v of 7b, the surfactant (360 mg) was first sonicated in a rosette cell at 0° C., in 8.55 mL of water. Next, the FDC (6 g) was added and the whole is sonicated, until optimal average particle size and size distribution are obtained. The emulsion was then divided into aliquots, stocked under inert atmosphere, sterilized for 8 min at 121° C. in an autoclave, then stored at 40° C. and monitored over time. The results are presented in FIG. 5.

EXAMPLE 26:

Formulation with 7b 1%, Lecithin 2% w/v; FDC 50% w/v

The same process but with a mixture of surfactants composed of 120 mg of 7b and 240 mg of natural egg-yolk lecithins (EYP) gave FDC emulsion with the following average particle sizes: 0.15 µm on preparation, 0.21 µm after sterilization and 0.32 µm after 30 days at 40° C. (respectively 0.19 µm, 0.23 µm and 0.45 µm for the emulsion prepared with EYP alone).

EXAMPLE 27:

Formulation with 7b 1%, Pluronic F-68 2% w/v; FDC 50% w/v

In the same conditions as in example 25, 120 mg of 7b and 240 mg of Pluronic F-68 and 6 g of FDC gave an emulsion with an average particle size of 0.29 µm at preparation, 0.29 µm after sterilization and 0.64 µm after 30 days at 40° C. (respectively 0.29 µm at preparation, and after sterilization compared to 0.62 µm for the emulsion prepared with Pluronic alone).

Emulsions prepared with the microfluidizer

EXAMPLE 28:

Formulation with 7b 1% w/v; Perfluorooctyl Bromide (Perflubron, PFOB) 90% w/v

To prepare 40 mL of a 90% w/v PFOB emulsion, surfactant 7b (400 mg) was first dispersed in 19.6 mL of a phosphate buffer with an Ultra Turrax. PFOB (36 g) was then added slowly and the whole was mixed for 10 min at 24000 revolutions/min. The resulting pre-emulsion was transferred into a microfluidizer and emulsified for 1 min at 800–1000 bar. The evolution of the average particle size over time at 40° C. are presented in FIG. 6.

EXAMPLE 29:

Formulation with 7b 0.5%, EYP 3.5% w/v; PFOB 90% w/v

This emulsion was prepared as for example 28 with 200 mg of 7b and 1.4 g of EYP for 35 g of PFOB. The ageing results are presented in FIG. 7.

The stabilizing effect obtained by employing the compounds of the invention is illustrated in FIG. 5: after a month at 40° C., the average particle sizes of the emulsions obtained are, even after sterilization, lower that those of the reference emulsions based on EYP alone.

The stabilizing power of these compounds is considerable compared to that of EYP, even when they are used in small proportions: thus an emulsion concentrated in fluorocarbon (90% w/v), here PFOB, prepared with only 1% w/v of compound 7b, is more stable than an emulsion containing 4% of EYP (see FIG. 6).

These compounds also present a strong stabilizing co-surfactant effect with EYP: in small amounts, in association with EYP, they facilitate the emulsification process (shorter emulsification times, smaller particle sizes), as illustrated in FIG. 7. Thus for a typical emulsion, incorporating 4% of EYP, the emulsification process is facilitated by replacing a minute quantity of the latter (⅛$^{th}$) by compound 7b; this significantly reduces the average particle size and causes strong stabilization.

There will be various modifications, improvements, and applications of the disclosed invention that will be apparent to those of skill in the art, and the present application is intended to cover such embodiments; therefore, it is intended that the full scope of these be measured by reference to the scope of the following claims.

What is claimed is:

1. A composition containing at least one compound of the formulas $$\underset{R^2}{\overset{R^1}{\diagdown}}CH-X-\overset{\overset{V}{\|}}{\underset{Z}{P}}\diagdown Y \quad \text{and} \quad \underset{R^3}{\overset{R^2}{\diagdown}}CH-(CH_2)_m-X-\overset{\overset{V}{\|}}{\underset{Z}{P}}\diagdown Y$$
$$\text{Ia} \qquad\qquad\qquad \text{Ib}$$

wherein

V is O or S; —X— is —O—; —S—; or —NR$^4$—; wherein

R$^4$ is a hydrogen atom; a linear or branched, saturated or unsaturated C$_1$ to C$_{24}$ hydrocarbon radical; or R$_F$(CH$_2$)$_a$ W; wherein a is an integer from 0 to 12;

R$_F$ is a fluorinated C$_2$ to C$_{24}$ alkyl radical; wherein 50 to 100% of the hydrogen atoms have been replaced by fluorine atoms, and R$_F$ can bear other substituents chosen from among Cl and Br, and R$_F$ includes at least 4 fluorine atoms; and W is —(CH=CH)$_d$—(CH$_2$)$_e$—(CH=CH)$_f$—(CH$_2$)$_g$—; wherein d is an integer from 0 to 12;

e is an integer from 0 to 11;

f is an integer from 0 to 12;

g is an integer from 0 to 11;

d+f=0 to 12; and e+g=0 to 11;

—OCH$_2$CH(CH$_2$OH)CH$_2$—; or

—OCH$_2$CH(CH$_2$OH)—; and m is an integer from 1 to 20;

R$^1$ represents a radical selected from the group consisting of:

R$_F$;

R$_F$—(CH$_2$)$_a$—W—A—(CH$_2$)$_b$—;

R$_F$—(CH$_2$CH$_2$O)$_c$—CH$_2$—;

R$_F$—(CH(CH$_3$)CH$_2$O)$_c$—CH$_2$—;

R$_F$—(CH$_2$CH$_2$S)$_c$—CH$_2$—; and

R$_F$—W—; wherein a, R$_F$ and W are as defined above, b is an integer from 1 to 12;

c is an integer from 1 to 12; and

A represents —O—; —S—; —OC(O)—; —C(O)O—; —(R$^5$) N—; or —(R$^5$) (R$^6$)N$^+$—; wherein R$^5$ and R$^6$ represent a hydrogen atom; a linear or branched, saturated or unsaturated C$_1$ to C$_{24}$ hydrocarbon radical; a hydroxyethyl radical; or the R$_F$(CH$_2$)$_a$W radical; wherein R$_F$, a, and W are as defined above;

—(CH$_2$)$_n$—; wherein n=0 or 1;

—C(O)N(R$^5$)—(CH$_2$)$_s$—B—, wherein

R$^5$ is as defined above;

s=1 to 12; and

B is —O—; —OC(O)— or —C(O)O—; —C(O)N(R$^7$) —(CH$_2$)$_r$— or —N(R$^7$)C(O)(CH$_2$)$_r$—; wherein r=1 to 12; and R$^7$ represents a hydrogen atom; a linear or branched, saturated or unsaturated C$_1$ to C$_{24}$ hydrocarbon radical; the hydroxyethyl radical; or the R$_F$(CH$_2$)$_a$—W— radical; wherein R$_F$, a, and W are as defined above.

R$^2$ represents a hydrogen atom;

R$^1$—;

R$_H$—W—A—(CH$_2$)$_b$—;

R$_H$—(CH$_2$CH$_2$O)$_c$—CH$_2$—;

R$_H$—(CH(CH$_3$)CH$_2$O)$_c$—CH$_2$—; or

R$_H$—(CH$_2$CH$_2$S)$_c$—CH$_2$—; wherein

R$_H$ represents a hydrogen atom; or a linear or branched, saturated or unsaturated C$_1$ to C$_{20}$ hydrocarbon chain; and W, A, b and c are as defined above.

R$^3$ represents a radical selected from the group consisting of:

R$_F$—;

R$_F$—(CH$_2$)$_a$—W—A—;

R$_F$(CH$_2$CH$_2$O)$_c$—;

R$_F$—(CH(CH$_3$)CH$_2$O)$_c$—;

R$_F$(CH$_2$CH$_2$S)$_c$—;

R$_F$—W—;

R$_H$—W—A—;

R$_H$(CH$_2$CH$_2$O)$_c$—;

R$_H$(CH(CH$_3$)CH$_2$O)$_c$—;

R$_H$(CH$_2$CH$_2$S)c—; wherein

R$_F$, a, W, A, c and R$_H$ are as defined above; provided that at least one of R$^2$ and R$^3$ of formula (Ib) bears the R$_F$ part;

Y represents a radical selected from the group consisting of:

—X$^1$(CH$_2$)$_{a'}$X$^2$(R$^8$); or

—X$^1$(R$^8$); wherein a' is an integer from 2 to 12;

X$^1$ and X$_2$ are independently —O—, —S— or —N(R$^9$)—; wherein

R$^9$ is a hydrogen atom; a linear or branched, saturated or unsaturated C$_1$ to C$_{24}$ hydrocarbon; and R$^8$ represents a radical derived from the group consisting of:

a sugar which is a tetrose, pentose, hexose, aminopentose, aminohexose, deoxypentose, deoxyhexose, disaccharide and oligosaccharide;

a cyclic hexitol, a polyol consisting of the hydrogenated form of a sugar of the tetrose, pentose, hexose, aminopentose, aminohexose, deoxypentose, deoxyhexose, disaccharide or oligosaccharide series; and a sugar or polyol as defined above; wherein one or several hydrogen atoms of the OH polyol or sugar groups have been replaced by an acetyl, benzyl, allyl, benzoyl, trityl, isopropylidene, benzylidene, or cyclohexylidene group;

by a group of formula (CH$_2$CH$_2$O)$_p$R$^9$; wherein p is an integer from 1 to 100; and R$^9$ is as defined above; or by an R$^1$ group as defined above;

$$\underset{R^{11}}{\overset{R^{10}}{\diagdown}}CH-X^1- \quad \text{or} \quad \underset{R^{11}}{\overset{R^{12}}{\diagdown}}CH-(CH_2)_m-X^1-$$

wherein m and X$^1$ are as defined above;

R$^{10}$ and R$^{11}$, which may be identical or different, represent R$^2$ as defined above; and $R^{12}$ represents $R^3$ as defined above;
—OH;
—OM; wherein M is an organic or inorganic cation;
—O(CH$_2$CH$_2$O)$_p$R$^9$;
—O(CH$_2$(CH$_3$)CH$_2$O)$_q$R$^9$; or
—O(CH$_2$CH$_2$O)$_q$—(CH(CH$_3$)CH$_2$O)$_{q'}$—(CH$_2$CH$_2$O)$_{q''}$R$^9$; wherein
R$^9$ is as defined above; and
p, q, q' and q" are integers from 1 to 100; and Z represents a radical selected from the group consisting of:
—X$^1$(CH$_2$)$_a$—X$^2$(R$^8$);
—X$^1$(R$^8$);
—OH;
—OM;
—O(CH$_2$CH$_2$O)$_p$R$^9$;
—O(CH(CH$_3$)CH$_2$O)$_q$R$^9$;
—O(CH$_2$CH$_2$O)$_q$—(CH(CH$_3$)CH$_2$O)$_{q'}$—(CH$_2$CH$_2$O)$_{q''}$—R$^9$;
—OCH$_2$CH(OH)CH$_2$OH,
—N(R$^{14}$)(R$^{15}$);
—O(CH$_2$)$_{d'}$—W'; and
X$^2$R$^{17}$ wherein X$^1$, X$^2$, R$^8$, R$^9$, a', p, q, q' and q" are as defined above;

R$^{14}$ and R$^{15}$ are independently a hydrogen atom;

a linear or branched C$_1$ to C$_4$ alkyl group; or (CH$_2$CH$_2$O)$_{b'}$R$^9$, wherein b' is an integer from 1 to 5; or R$^{14}$ and R$^{15}$ together form —(CH$_2$)$_{c'}$, wherein c' is an integer from 2 to 5; or R$_{14}$ and R$_{15}$ together form with the nitrogen atom a morpholino group;

W' represents an acetic 2-amino group;

—N(R$^{14}$)(R$^{15}$); or —N$^+$(R$^{14}$)(R$^{15}$)(R$^{16}$); wherein

R$^{14}$ and R$^{15}$ are as defined above; and

R$^{16}$ is independently selected from the group consisting of R$^{14}$ as defined above and radicals derived from an active therapeutic agent;

d' is an integer from 1 to 5; and

R$^{17}$ is a radical derived from a pharmaceutically active molecule;

provided that: Y and Z do not both represent —OH; —OM or —O(CH$_2$CH$_2$O)$_p$R$^9$ wherein p=1 to 5; and Z does not represent
—OH; —OM;
—N(R$^{14}$)(R$^{15}$);
—O—(CH$_2$)$_{d'}$—W'; or
—OCH$_2$—CH(OH)—CH$_2$OH;
when Y is

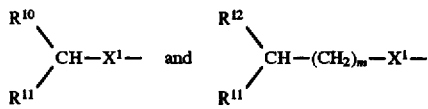

and Z is not
—N(R$^{14}$)(R$^{15}$);
—O—(CH$_2$)d'—W'; or
—O—CH$_2$—(CHOH)—CH$_2$OH;

when Y is OH; OM; or O(CH$_2$CH$_2$O)$_p$R$^9$ wherein p=1 to 5;

wherein said compound is incorporated into natural or synthetic vesicles or liposomes.

2. A composition according to claim 1 which carries an active principal.

3. A vesicular or liposomal composition according to claim 1, wherein said vesicles or liposomes comprise perfluoroalkylated phospholipids.

4. A vesicle or liposome comprising a compound selected from the group consisting of:
(2-(F-hexyl)ethyl)(6-D-glucosyl)phosphate,
(2-(F-octyl)ethyl)(6-D-glucosyl)phosphate,
(5-(F-hexyl)pentyl)(6-D-glucosyl)phosphate,
(5-(F-octyl)pentyl)(6-D-glucosyl)phosphate,
(2-(F-hexyl)ethyl)(6-D-galactosyl)phosphate,
(2-(F-octyl)ethyl)(6-D-galactosyl)phosphate,
(5-(F-hexyl)pentyl)(6-D-galactosyl)phosphate,
(5-(F-octyl)pentyl)(6-D-galactosyl)phosphate,
(2-(F-hexyl)ethyl)(6-D-mannosyl)phosphate,
(2-(F-octyl)ethyl)(6-D-mannosyl)phosphate,
(5-(F-hexyl)pentyl)(6-D-mannosyl)phosphate,
(5-(F-octyl)pentyl)(6-D-mannosyl)phosphate,
(11-(F-hexyl)undecyl)(6-D-glucosyl)phosphate,
(11-(F-octyl)undecyl)(6-D-glucosyl)phosphate,
(11-(F-hexyl)undecyl)(6-D-galactosyl)phosphate,
(11-(F-octyl)undecyl)(6-D-galactosyl)phosphate,
(11-(F-hexyl)undecyl)(6-D-mannosyl)phosphate,
(11-(F-octyl)undecyl)(6-D-mannosyl)phosphate,
(5-(F-hexyl)-4-pentenyl)(6-D-glucosyl)phosphate,
(5-(F-octyl)-4-pentenyl)(3-D-glucosyl)phosphate,
(5-(F-octyl)-4-pentenyl)(6-D-galactosyl), phosphate,
(1-(2-(F-hexyl)ethyl)decyl)(6-D-glucosyl) phosphate,
(1-(2-(F-octyl)ethyl)decyl)(6-D-glucosyl) phosphate,
(1-(5-(F-hexyl)pentyl)decyl)(6-D-glucosyl) phosphate,
(1-(10-(F-octyl)decyl)decyl)(6-D-glucosyl) phosphate,
(1-(2-(F-hexyl)ethyl)decyl)(6-D-galactosyl) phosphate,
(1-(2-(F-octyl)ethyl)decyl)(6-D-galactosyl) phosphate,
(1-(5-(F-hexyl)pentyl)decyl)(6-D-galactosyl) phosphate,
(1-(10-(F-octyl)decyl)decyl)(6-D-galactosyl) phosphate,
(1-(2-(F-hexyl)ethyl)decyl)(6-D-mannosyl)phosphate,
(1-(2-(F-octyl)ethyl)decyl)(6-D-mannosyl)phosphate,
(1-(5-(F-hexyl)pentyl)decyl)(6-D-mannosyl) phosphate,
(1-(10-(F-octyl)decyl)decyl)(6-D-mannosyl) phosphate,
(1-(2-(F-hexyl)ethyl)dodecyl)(6-D-glucosyl) phosphate,
(1-(2-(F-octyl)ethyl)dodecyl)(6-D-glucosyl) phosphate,
(1-(2-(F-octyl)ethyl)tetradecyl)(6-D-glucosyl) phosphate,
(1-(2-(F-octyl)ethyl)tetradecyl)(6-D galactosyl)phosphate,
(2-(F-hexyl)ethyl)(3-D-glucosyl)phosphate,
(2-(F-octyl)ethyl)(3-D-glucosyl)phosphate,
(1-(2-(F-octyl)ethyl)decyl)(3-D-glucosyl) phosphate,
1-(2-(F-octyl)ethyl)dodecyl)(3-D-glucosyl) phosphate,
1,3-di-O-(3-(F-octyl)propanoyl)-2-glyceryl)(6-D-glucosyl) phosphate,
(1,3-di-O-(5-(F-octyl)pentanoyl)-2-glyceryl)(6-D-glucosyl) phosphate,
(1,3-di-O-(5-(F-octyl)pentyl)-2-glyceryl)(6-D-glucosyl) phosphate,
(1,3-di-O-(5-(F-octyl)pentyl)-2-glyceryl)(3-D-glucosyl) phosphate; and
(2-(F-octyl)ethyl)(5-xylityl)phosphate, in organic or inorganic salt form.

* * * * *